(12) United States Patent
Chen et al.

(10) Patent No.: US 7,432,414 B2
(45) Date of Patent: Oct. 7, 2008

(54) TRANSGENIC MOUSE HAVING AN AMYLOID PRECURSOR PROTEIN WITH A MODIFIED BETA SECRETASE CLEAVAGE SITE

(75) Inventors: Richard Z. Chen, Scotch Plains, NJ (US); Adam J. Simon, Langhorne, PA (US); Thomas F. Vogt, Princeton, NJ (US)

(73) Assignee: Merck & Co., Inc., Rahway, NJ (US)

( * ) Notice: Subject to any disclaimer, the term of this patent is extended or adjusted under 35 U.S.C. 154(b) by 177 days.

(21) Appl. No.: 10/558,656

(22) PCT Filed: May 28, 2004

(86) PCT No.: PCT/US2004/016836

§ 371 (c)(1),
(2), (4) Date: Nov. 29, 2005

(87) PCT Pub. No.: WO2004/111189

PCT Pub. Date: Dec. 23, 2004

(65) Prior Publication Data

US 2007/0101449 A1    May 3, 2007

(51) Int. Cl.
*A01K 67/027* (2006.01)
*G01N 33/00* (2006.01)
(52) U.S. Cl. ............................... 800/18; 800/3; 800/12
(58) Field of Classification Search ................... None
See application file for complete search history.

(56) References Cited

U.S. PATENT DOCUMENTS

| | | | |
|---|---|---|---|
| 6,187,992 B1 | 2/2001 | Zheng et al. | |
| 7,132,401 B2 | 11/2006 | Brady et al. | |
| 7,196,163 B2 * | 3/2007 | Hazuda et al. | 530/330 |
| 2007/0184488 A1 | 8/2007 | Brady et al. | |
| 2007/0219354 A1 | 9/2007 | Hazuda et al. | |

FOREIGN PATENT DOCUMENTS

| | | |
|---|---|---|
| WO | WO 89/06689 | 7/1989 |
| WO | WO 89/06693 | 7/1989 |

OTHER PUBLICATIONS

Holcomb et al. Accelerated Alzheimer-Type Phenotype in Transgenic Mice Carrying Both Mutant Amyloid Percursor Protein and Presenilin 1 Transgenes. Nature Medicine. Jan. 1998, vol. 4, pp. 97-100.*
Jantzen et al. Microglial Activation and β-Amyloid Deposit Reduction Caused by a Nitric Oxide-Releasing Nonsteroidal Anti-Inflammatory Drug in Amyloid Percursor Protein Plus Presenilin-1 Transgenic Mice. J. Neuroscience, Mar. 2002, vol. 22, pp. 2246-2254.*

Roberds et al. BACE Knockout Mice are Healthy Despite Lacking the Primary β-Secretase Activity in Brain: Implications for Alzheimer's Disease Therapeutics. Human Molec. Genet., 2001, vol. 10, pp. 1317-1324.*
Reaume et al. Enhanced Amyloidogenic Processing of the β-Amyloid Precursor Protein in Gene-Targeted Mice Bearing the Swedish Familial Alzheimer's Disease Mutations and a "Humanized" Aβ Sequence. J. Biol. Chem., 1996, vol. 271, pp. 23380-23388.*
Echeverria et al. Rat Transgenic Models with Phenotype of Intracellular A-Beta Accumulation in Hippocampus and Cortex. J.Alzheimer's Disease. 2004, vol. 6, pp. 209-219.*
Dudal et al. Inflammation Occurs Early During the A-Beta Deposition Process in TgCRND8 Mice. Neurobiol. Aging. 2004, vol. 25, pp. 861-871.*
Prelle, K. et al. Establishment of Pluripotent Cell Lines from Vertebrate Species—Present Status and Future Prospects. Cells Tissues Organs. 1999, vol. 165, pp. 220-236.*
Wheeler, M. B. et al. Transgenic Technology and Applications in Swine. Theriogenelogy. 2001, vol. 56, pp. 1345-1369.*
Moreadith, R. W. Gene Targeting in Embryonic Stem Cells: the New Physiology and Metabolism. J. Molecular Med. 1997, vol. 75, pp. 208-216.*
Cai, et al., "BACE1 is the major β-secretase for generation of Aβ peptides by neurons," Nature Neuroscience, vol. 4, No. 3, Mar. 2001, pp. 233-234.
Chartier-Harlin, "Early-onset Alzheimer's disease caused by mutations at codon 717 of the β-amyloid precursor protein gene," Letters to Nature, vol. 353, Oct. 31, 1991, pp. 844-846.
Chishti, et al., "Early-onset Amyloid Deposition and Cognitive Deficits in Transgenic Mice Expressing a Double Mutant Form of Amyloid Precursor Protein 695*," Journal of Biological Chemistry, vol. 276, No. 24, Jun. 15, 2001, pp. 21562-21570.
Citron, et al, "Mutation of the β-amyloid precursor protein in familial Alzheimer's disease increases β-protein production," Nature, vol. 360, Dec. 17, 1992, pp. 672-674.
Citron, et al., "Generation of Amyloid β Protein from Its Precursor Is Sequence Specific," Neuron, vol. 14, Mar. 1995, pp. 661-670.
Duff, et al., "Increased amyloid-β42(43) in brains of mice expressing mutant presenilin 1," Nature, vol. 383, Oct. 24, 1996, pp. 710-713.
Holcomb, et al, "Accelerated Alzheimer-type phenotype in transgenic mice carrying both mutant amyloid precursor protein and presenilin 1 transgenes," Nature Medicine, vol. 4, No. 1, Jan. 1998, pp. 97-100.

(Continued)

*Primary Examiner*—Deborah Crouch
(74) *Attorney, Agent, or Firm*—Joan E. Switzer; William Krovatin

(57) ABSTRACT

The present invention provides transgenic animals having an amyloid precursor protein wherein the amino acids flanking the &bgr; secretase cleavage site are NF and EV. The invention also provides tissues and cell lines derived from such animals. The invention further provides methods of screening candidate compounds to determine whether the compounds can alter the rate of cleavage of amyloid precursor protein by &bgr; secretase.

18 Claims, 10 Drawing Sheets

OTHER PUBLICATIONS

Feng, et al.,"Deficient Neurogenesis in Forebrain-Specific Presenilin-1 Knockout Mice Is Associated with Reduced Clearance of Hippocampal Memory Traces," Neuron, vol. 32, Dec. 6, 2001, pp. 911-926.

Games, et al., "Alzheimer-type neuropathology in transgenic mice overexpressing V717F β-amyloid precursor protein," Nature, vol. 373, Feb. 9, 1995, pp. 523-527.

Geula, et al., "Aging renders the brain vulnerable to amyloid β-protein neurotoxicity," Nature Medicine, vol. 4, No. 7, Jul. 1998, pp. 827-831.

Giasson, et al., "Neuronal α-Synucleinopathy with Severe Movement Disorder in mice Expressing A53T Human α-Synuclein," Neuron, vol. 34, May 16, 2002, pp. 521-533.

Ghosh, et al., 'Design of Potent Inhibitors for Human Brain Memapsin 2 (β-Secretase), J. Am. Chem. Soc., vol. 122, 2000, pp. 3522-3523.

Gotz, et al, "Formation of Neurofibrillary Tangles in P301L Tau Transgenic Mice Induced by Aβ42 Fibrils," Science, vol. 293, Aug. 24, 2001, pp. 1491-1495.

Hsiao et al., "Correlative Memory Deficits, Aβ Elevation, and Amyloid Plaques in Transgenic Mice," Science, vol. 274, Oct. 4, 1996, pp. 99-102.

Hussain, et al., "Identification of a Novel Aspartic Protease (ASP-2) as β-Secretase," Molecular and Cellular Neuroscience, vol. 14, 1999, pp. 419-427.

Jarrett, et al., "The Carboxy Terminus of the β Amyloid Protein Is Critical for the Seeding of Amyloid Formation: Implications for the Pathogenesis of Alzheimer's Disease," Biochemistry, vol. 32, No. 18, May 11, 1993, pp. 4693-4697.

Jin, et al., "Transgenic Mice Over-Expressing the C-99 Fragment of βPP with an α-Secretase Site Mutation Develop a Myopathy Similar to Human Inclusion Body Myositis," American Journal of Pathology, vol. 153, No. 6, Dec. 1998, pp. 1679-1686.

Kang, et al., "The precursor of Alzheimer's disease amyloid A4 protein resembles a cell-surface receptor," Nature, vol. 325, Feb. 19, 1987, pp. 733-736.

Kitaguchi, et al., Novel precursor of Alzheimer's disease amyloid protein shows protease inhibitory activity, Nature, vol. 331, Feb. 11, 1988, pp. 530-532.

LaFerla, et al., "The Alzheimer's Aβ peptide induces neurodegeneration and apoptotic cell death in transgenic mice," Nature Genetics, vol. 9, Jan. 1995, pp. 21-30.

Lamb, et al., "Introduction and expression of the 400 kilobase precursor amyloid protein gene in transgenic mice," Nature Genetics, vol. 5, Sep. 1993, pp. 22-30.

Lewis, et al., "Enhanced Neurofibrillary Degeneration in Transgenic Mice Expressing Mutant Tau and APP," Science, vol. 293, Aug. 24, 2001, pp. 1487-1491.

Lin, et al., "Human aspartic protease memapsin 2 cleaves the β-secretase site of β-amyloid precursor protein," PNAS, vol. 97, No. 4, Feb. 15, 2000, pp. 1456-1460.

Masliah, et al., "β-Amyloid peptides enhance a-synuclein accumulation and neuronal deficits in a transgenic mouse model linking Alzheimer's disease and Parkinson's disease," PNAS, Oct. 9, 2001, Vo.. 98, No. 21, pp. 12245-12250.

Mattson, et al., "b-Amyloid Peptides Destabilize Calcium Homeostasis and Render Human Cortical Neurons Vulnerable to Excitotoxicity," Journal of Neuroscience, vol. 12, No. 2, Feb. 1992, pp. 376-389.

Mullan, et al., "A Pathogenic mutation for probably Alzheimer's disease in the APP gene at the N-terminus of β-amyloid," Nature Genetics, vol. 1, Aug. 1992, pp. 345-347.

Murrell, et al., "A Mutation in the Amyloid Precursor Protein Associated with Hereditary Alzheimmer's Disease," Science, vol. 254, Oct. 4, 1991, pp. 97-99.

Ponte, et al., "A new A4 amyloid mRNA contains a domain homologous to serine proteinase inhibitors," Nature, vol. 331, Feb. 11, 1988, pp. 525-527.

Scheuner, et al., "Secreted amyloid β-protein similar to that in the senile plaques of Alzheimer's disease is increased in vivo by the presenilin 1 and 2 and AP mutations linked to familial Alzheimer's disease," Nature Medicine, vol. 2, No. 8, Aug. 1996, pp. 864-870.

Sinha, et al., "Purification and cloning of amyloid precursor protein β-secretase from human brain," Nature, vol. 402, Dec. 1999, pp. 537-540.

Sisodia, et al., "b-Amyloid precursor protein cleavage by a membrane-bound protease,"PNAS, vol. 89, Jul. 1992, pp. 6075-6079.

Vassar, et al., "β-Secretase Cleavage of Alzheimer's Amyloid Precursor Protein by the Transmembrane Aspartic Protease BACE," Science, vol. 286, Oct. 22, 1999, pp. 735-741.

Yan, et al., "Membrane-anchored aspartyl protease with Alzheimer's disease b-secretase actitivity," Nature, vol. 402, Dec. 2, 1999, pp. 533-537.

Yanker, et al., "Neutotrophic and Neurotoxic Effects of Amyloid B Protein: Reversal by Tachykinin Neuropeptiodes," Science, vol. 250, Oct. 12, 1990, pp. 279-250.

Zheng, et al., "B-Amyloid Precursor Protein-Deficient Mice Show Reactive Gliosis and Decreased Locomotor Activity," Cell., vol. 81, May 19, 1995, pp. 525-531.

* cited by examiner

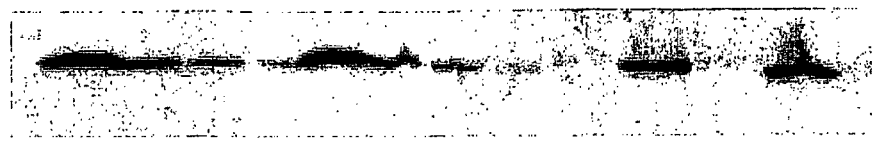
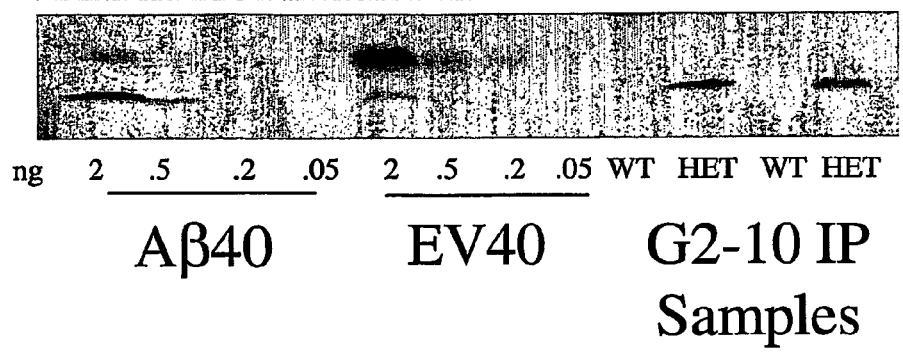
FIGURE 1

YAC = WT hAPP-Yeast Artificial Chromosome
Het = WP-hAPP KI heterozygote
WT = Wild type litter mates

FIGURES 5A & B

TRANSGENIC MOUSE HAVING AN AMYLOID PRECURSOR PROTEIN WITH A MODIFIED BETA SECRETASE CLEAVAGE SITE

FIELD OF THE INVENTION

The present invention is directed to the field of Alzheimer's disease. In particular, the present invention provides transgenic animals having an amyloid precursor protein with a modified β secretase cleavage site. The invention also provides novel methods of identifying substances that are specific inhibitors of the cleavage of amyloid precursor protein by β secretase.

BACKGROUND OF THE INVENTION

Alzheimer's disease is a common, chronic neurodegenerative disease, characterized by a progressive loss of memory and sometimes-severe behavioral abnormalities, as well as an impairment of other cognitive functions that often leads to dementia and death. It ranks as the fourth leading cause of death in industrialized societies after heart disease, cancer, and stroke. The incidence of Alzheimer's disease is high, with an estimated 2.5 to 4 million patients affected in the United States and perhaps 17 to 25 million worldwide. Moreover, the number of sufferers is expected to grow as the population ages.

A characteristic feature of Alzheimer's disease is the presence of large numbers of insoluble deposits, known as amyloid plaques, in the brains of those affected. Autopsies have shown that amyloid plaques are found in the brains of virtually all Alzheimer's patients and that the degree of amyloid plaque deposition correlates with the degree of dementia (Cummings & Cotman, 1995, Lancet 326:1524-1587). While some opinion holds that amyloid plaques are a late stage by-product of the disease process, the consensus view is that amyloid plaques and/or soluble aggregates of amyloid peptides are more likely to be intimately, and perhaps causally, involved in Alzheimer's disease.

A body of published experimental evidence supports this view. For example, amyloid β-protein ("Aβ"), a primary component of amyloid plaques, is toxic to neurons in culture and transgenic mice that overproduce Aβ in their brains show significant deposition of Aβ into amyloid plaques as well as significant neuronal toxicity (Yankner, 1990, Science 250: 279-282; Mattson et al., 1992, J. Neurosci. 12:379-389; Games et al., 1995, Nature 373(6514):523-527; LaFerla et al., 1995, Nature Genetics 9:21-29). Mutations in the APP gene, leading to increased Aβ production, have been linked to heritable forms of Alzheimer's disease (Goate et al., 1991, Nature 349:704-706; Chartier-Harlan et al., 1991, Nature 353:844-846; Murrel et al., 1991, Science 254:97-99; Mullan et al., 1992, Nature Genetics 1:345-347). Presenilin-1 (PS1) and presenilin-2 (PS2) related familial early-onset Alzheimer's disease (FAD) shows disproportionately increased production of Aβ1-42, the 42 amino acid isoform of Aβ, as opposed to Aβ1-40, the 40 amino acid isoform (Scheuner et al, 1996, Nature Medicine 2:864-870). The longer isoform of Aβ is more prone to aggregation than the shorter isoform (Jarrett et al, 1993, Biochemistry 32:4693-4697). Injection of the insoluble, fibrillar form of Aβ into monkey brains results in the development of pathology (neuronal destruction, tau phosphorylation, microglial proliferation) that closely mimics Alzheimer's disease in humans (Geula et al., 1998, Nature Medicine 4:827-831). See Selkoe, 1994, J. Neuropathol. Exp. Neurol. 53:438-447; Hardy and Selkoe, 2002, Science 297 (5580) 353-6; for reviews of the evidence that amyloid plaques have a central role in Alzheimer's disease.

APP is a ubiquitous membrane-spanning (type 1) glycoprotein that undergoes a variety of proteolytic processing events. (Selkoe, 1998, Trends Cell Biol. 8:447-453). APP is actually a family of polypeptides produced by alternative splicing from a single gene. Major forms of APP are known as $APP_{695}$, $APP_{751}$, and $APP_{770}$, with the subscripts referring to the number of amino acids in each splice variant (Ponte et al., 1988, Nature 331:525-527; Tanzi et al., 1988, Nature 331: 528-530; Kitaguchi et al., 1988, Nature 331:530-532).

Aβ, a 38-43 amino acid peptide derived by proteolytic cleavage of the amyloid precursor protein (APP), is the major component of amyloid plaques (Glenner & Wong, 1984, Biochem. Biophys. Res. Comm. 120:885-890). APP is expressed and constitutively catabolized in most cells. APP has a short half-life and is metabolized rapidly down two pathways. In one pathway, cleavage by an enzyme known as α secretase occurs while APP is still in the trans-Golgi secretory compartment (Kuentzel et al., 1993, Biochem. J. 295:367-378). This cleavage by α secretase occurs within the Aβ portion of APP, thus precluding the formation of Aβ.

In contrast to this non-amyloidogenic pathway involving α secretase described above, proteolytic processing of APP by β secretase exposes the N-terminus of Aβ, which after γ secretase cleavage at the variable C-terminus, liberates Aβ. This Aβ-producing pathway involves cleavage of the Met671-Asp672 bond (numbered according to the 770 amino acid isoform) by β secretase. The C-terminus is actually a heterogeneous collection of cleavage sites rather than a single site since γ secretase activity occurs over a short stretch of APP amino acids rather than at a single peptide bond. Peptides of 40 or 42 amino acids in length (Aβ1-40 and Aβ1-42, respectively) predominate among the C-termini generated by γ secretase, however, a recent report suggests 1-38 is a dominant species in cerebrospinal fluid. (J. Wiltfang et al, unpublished, presented at International Congress of Alzheimer Disease, July 2002, Stockholm, Sweden). Aβ1-42 is more prone to aggregation than Aβ1-40, the major component of amyloid plaque (Jarrett et al., 1993, Biochemistry 32:4693-4697; Kuo et al., 1996, J. Biol. Chem 271:4077-4081), and its production is closely associated with the development of Alzheimer's disease (Sinha & Lieberburg, 1999, Proc. Natl. Acad. Sci. USA 96:11049-11053). The bond cleaved by γ secretase appears to be situated within the transmembrane domain of APP. It is unclear as to whether the C-termini of Aβ1-40 and A 1-42 are generated by a single γ secretase protease with relaxed specificity or by two distinct proteases. For a review that discusses APP and its processing, see Selkoe, 1998, Trends Cell. Biol. 8:447-453. In the amyloidogenic pathway, APP is cleaved by β secretase to liberate sAPPβ and CTFβ, which CTFβ is then cleaved by γ secretase to liberate the harmful Aβ peptide.

While abundant evidence suggests that extracellular accumulation and deposition of Aβ is a central event in the etiology of AD, recent studies have also proposed that increased intracellular accumulation of Aβ or amyloid containing C-terminal fragments may play a role in the pathophysiology of AD. For example, over-expression of APP harboring mutations which cause familial Aβ results in the increased intracellular accumulation of CTFβ in neuronal cultures and Aβ42 in HEK 293 cells. Aβ42 is the 42 amino acid long form of Aβ that is believed to be more potent in forming amyloid plaques than the shorter forms of Aβ. Moreover, evidence suggests that intra- and extracellular Aβ are formed in distinct cellular pools in hippocampal neurons and that a common feature associated with two types of familial AD mutations in APP ("Swedish" and "London") is an increased intracellular accumulation of Aβ$_{42}$. Thus, based on these studies and earlier reports implicating extracellular Aβ accumulation in AD pathology, it appears that altered APP catabolism may be involved in disease progression.

Of key importance in this Aβ-producing pathway is the position of the γ secretase cleavage. If the γ secretase proteolytic cut is at residue 711-712, short Aβ (Aβ40) is the result; if it is a proteolytic cut after residue 713, long Aβ (Aβ42) is the result. Thus, the γ secretase process is central to the production of Aβ peptide of 40 or 42 amino acids in length (Aβ40 and Aβ42, respectively). For a review that discusses APP and its processing, see Selkoe, 1998, Trends Cell. Biol. 8:447-453; Selkoe, 1994, Ann. Rev. Cell Biol. 10:373-403. See also, Esch et al., 1994, Science 248:1122.

Reports show that soluble β-amyloid peptide is produced by healthy cells into culture media (Haass et al., 1992, Nature 359:322-325) and in human and animal CSF (Seubert et al., 1992, Nature 359:325-327).

Cleavage of APP can be detected in a number of convenient manners, including the detection of polypeptide or peptide fragments produced by proteolysis. Such fragments can be detected by any convenient means, such as by antibody binding. Another convenient method for detecting proteolytic cleavage is through the use of a chromogenic β secretase substrate whereby cleavage of the substrate releases a chromogen, e.g., a colored or fluorescent, product. More detailed analyses can be performed including mass spectroscopy.

As noted above, various naturally occurring mutations in APP have been identified that lead to familial, early-onset Alzheimer's disease. Once such mutation, known as the "Swedish" mutation, consists of a double change in the amino acid sequence of APP$_{695}$ at the β secretase cleavage site: K$^{595}$, M$^{596}$ to N$^{595}$, L$^{596}$ (Mullan et al., 1992, Nature Genet. 1:345; Citron et al., 1992, Nature 360:672). cultured cells that express a cDNA encoding APP bearing the Swedish version of the β secretase cleavage site produce about 6-8 fold more Aβ than cells expressing wild-type APP (Citron et al., 1992, Nature 360:672-674).

Citron et al., 1995. Neuron 14:661-670 varied the amino acid sequence at the β secretase cleavage site of APP (positions Val594-Ala598 of APP$_{695}$) and found that most substitutions in this sequence strongly decreased or eliminated cleavage by β secretase. Only the Swedish mutation was found to strongly increase cleavage.

Sisodia, 1992, Proc. Natl. Acad. Sci. USA 89(13): 6075-6079.described experiments in which various changes in the amino acid sequence of APP in the region of the βsecretase cleavage site were made and the effect of those changes on cleavage by βsecretase were measured. A change of K to V at position 612 of the 695 amino acid version of APP led to reduced cleavage by βsecretase. The K612V change has been built into a vector encoding the carboxy terminal 99 amino acids of APP and transgenic mice expressing this construct have been obtained. Such mice develop a myopathy similar to human inclusion body myositis (Jin et al., 1998, Am. J. Pathol. 153:1679-1686).

Much interest has focused on the possibility of inhibiting the development of amyloid plaques as a means of preventing or ameliorating the symptoms of Alzheimer's disease. To that end, a promising strategy is to inhibit the activity of β- and γ secretase, the two enzymes that together are responsible for producing Aβ. This strategy is attractive because, if amyloid plaque formation as a result of Aβ deposition is a cause of Alzheimer's disease, then inhibiting the activity of one or both of the two secretases would intervene in the disease process at an early stage, before late-stage events such as inflammation or apoptosis occur. Such early stage intervention is expected to be particularly beneficial (see, e.g., Citron, 2000, Molecular Medicine Today 6:392-397).

To that end, various assays have been developed that are directed to the identification of substances that may interfere with the production of Aβ or its deposition into amyloid plaques. U.S. Pat. No. 5,441,870 is directed to methods of monitoring the processing of APP by detecting the production of amino terminal fragments of APP. U.S. Pat. No. 5,605,811 is directed to methods of identifying inhibitors of the production of amino terminal fragments of APP. U.S. Pat. No. 5,593, 846 is directed to methods of detecting soluble Aβ by the use of binding substances such as antibodies. Esler et al., 1997, Nature Biotechnology 15:258-263 described an assay that monitored the deposition of Aβ from solution onto a synthetic analogue of an amyloid plaque. The assay was suitable for identifying substances that could inhibit the deposition of Aβ. However, this assay is not suitable for identifying substances, such as inhibitors of β- or γ secretase, that would prevent the formation of Aβ.

Various groups have cloned and sequenced cDNA encoding a protein that is believed to be β secretase (Vassar et al., 1999, Science 286:735-741; Hussain et al., 1999, Mol. Cell. Neurosci. 14:419-427; Yan et al., 1999, Nature 402:533-537; Sinha et al., 1999, Nature 402:537-540; Lin et al., 2000, Proc. Natl. Acad. Sci. USA 97:1456-1460). Hong et al., 2000, Science 290:150-153 determined the crystal structure of the protease domain of human β secretase complexed with an eight-residue peptide-like inhibitor at 1.9 angstrom resolution. Compared to other human aspartyl proteases, the active site of human β secretase is more open and less hydrophobic, contributing to the broad substrate specificity of human β secretase (Lin et al., 2000, Proc. Natl. Acad. Sci. USA 97:1456-1460).

Ghosh et al., 2000, J. Am. Chem. Soc. 122:3522-3523 disclosed two inhibitors of β secretase, OM99-1 and OM99-2, that are modified peptides based on the β secretase cleavage site of the Swedish mutation of APP (SEVNL/DAEFR (SEQ ID NO: 1), with "/" indicating the site of cleavage). OM99-1 has the structure VNL*AAEF (SEQ ID NO: 2) (with "L*A" indicating the uncleavable hydroxyethylene transition-state isostere of the LA peptide bond) and exhibits a K$_i$ towards recombinant β secretase produced in *E. coli* of approximately 68+/-3 nM. OM99-2 has the structure EVNL*AAEF (SEQ ID NO: 3) (with "L*A" indicating the uncleavable hydroxyethylene transition-state isostere of the LA peptide bond) and exhibits a K$_i$ towards recombinant β secretase produced in *E. coli* of 96±3 nM. OM99-1 and OM99-2, as well as related substances, are described in International Patent Publication WO 01/00665.

A recent report indicates that β secretase inhibitors can act at micromolar levels in cell culture (Hom et al, J. Med Chem Letters, published online JM0256191, April 2003). Despite progress in identifying β secretase inhibitors, there are currently no approved pharmaceuticals for the treatment or prevention of Alzheimer's disease that are believed to exert their therapeutic effect through the inhibition of β secretase. Thus, there remains a need for additional assays that can be used to identify additional inhibitors of β secretase.

It is well known in the art that transgenic and genetically engineered animal models are useful for both basic and applied research in the field of Alzheimer's Disease research. Many human genetic mutations have been discovered through linkage and association analysis. These human alleles have been engineered into several animal models and serve as the basis of much of the in vivo research performed in the field. Among the most prevalent animal models are the PDAPP mouse (Games et al, 1995, Nature 373(6514):523-7) which encodes the V717F mutation in APP, the Tg2576 APPsw mouse encoding the Swedish mutation in APP (Hsiao et al, 1996, Science 274 (5283):99-102.) and mutant presenilin 1 transgenics (Duff et al, 1996, Nature 24:383(6603):710-3)). Each of these mice have enabled study of aspects of the processing of APP in vivo. In particular, the Tg2576 mouse model develops plaque pathology and is now a standard model for preclinical investigations of the amyloidosis process. The T2576 mouse model is often used in conjunction with behavioral and cognitive deficit studies. In addition to the Tg2576 mouse model, several YAC models have been created to more accurately reflect the appropriate regulatory elements (Lamb et al, 1993, Nature Genetics 5(1):22-30). In addition to these gain-of-function animal models there are several loss-of-function Knock-out (KO) animal models including PS1 KO (Feng et al., 2001, Neuron 32(5):911-26), BACE1 KO (Cai et al., 2001, Nature Neuroscience (3):2334), ADAM10 KO and APP KO (Zheng et al, 1995, Cell 81(4) 525-31). In addition to APP and Presenilin mutations, several groups have also created Tau transgenic animals. The P301L Tau mutant mice of Gotz et al (see Gotz et al., 2001, Science 293 (5534): 1491-5) and Lewis et al., 2000, Nature Genetics (4):402-5) are examples. Additionally, others have created α-synuclein transgenic animal models, including the A53T mutant mice (Giasson, 2002, Neuron 34(4):521-33).

Although each animal model is useful alone, they are often more useful when cross-bred in combination with other genetically engineered and transgenic models. Several prevalent cross-breeds include the Tg2576 ×PSI mouse (Duff et al. 1988, Nature Medicine 4 (1): 97-100) and the TgCRND8model encoding the combination of APPsw and V717F (Chishti et al, 2001, J. Biol. Chem. 276(24):21562-70). Moreover, there are bi-genic models which include APPsw ×P301L Tau (Lewis et al, 2001, Science 293 (5534): 1487-91) and APPsw ×A53T (Masliah, 2001, Proc. Natl Acad Sci USA 98(21):12245-12250). Finally, the recent emergence of triple transgenics animals, including the APPsw ×P301L ×PS1 model (F. LaFerla et al unpublished, presented at 6th International AD/PD conference, May 8-12, 2003, Seville, Spain) and Swedish/Dutch/Iowa triple transgenic (W. B. van Nostrand, Stony Brook, unpublished, presented at 6th International AD/PD conference, May 8-12, 2003, Seville, Spain) provides the ability to work with models systems that approximate aspects of particular disease states. The bi-genic and tri-genic animals are exemplary of the possible combinations that one can create by crossing the animals of the present invention to create models relevant to finding a medical treatment for Alzheimer's Disease.

Improved animal models for human Alzheimer Disease advance both mechanistic understanding and preclinical therapeutic validations. A number of useful animal models for Alzheimer Disease have been produced but the majority do not accurately reproduce the spatial and temporal expression of amyloid precursor protein over the lifetime of the animal. Such model systems often produce supra-physiological levels of the full length amyloid substrate protein, upon which the various proteolytic enzymes operate. The overexpression of APP and the reliance of many models on heterologous promotors may possibly confound potential feedback loops that operate on the modulation of APP gene expression. To more closely model the endogenous spatial and temporal expression patterns and natural history of amyloid pathophysiology, we have used gene-targeting in mouse embryonic stem cells to modify the mouse APP protein at the endogenous APP genetic locus. Thus the present invention provides an animal model of Alzheimer Disease which exhibits a wild-type pattern of APP expression while providing important phenotypes including a significant enhancement of beta-secretase site cleavage, an increased ratio of beta-secretase activity to alpha secretase activity and elevated amyloid production.

SUMMARY OF THE INVENTION

The present invention provides transgenic non-human animals in which the amyloid precursor protein is modified at the β secretase cleavage site to the sequence NFEV (SEQ ID NO: 4). The invention also features methods of using these animals and cells and tissues derived therefrom in identifying inhibitors of β secretase. A striking feature of the transgenic animals disclosed herein is that the novel cleavage site provides a superior in vivo substrate for β secretase than the wild type substrate. The modified substrate is cleaved in vivo by β secretase at a rate higher than that attending the wild-type and thus results in more cleaved product in a given time than similar substrates having the wild-type sequence.

An aspect of the present invention provides recombinant DNA molecules useful for constructing transgenic animals. These molecules include those providing a transgene encoding an APP polypeptide with the modified β secretase site NFEV (SEQ ID NO: 4). In particular embodiments, the targeting vectors can be knock-in vectors. In other embodiments, the vector can introduce the transgene at a location other that the endogenous APP gene. In particular embodiments the vector includes regulatory elements operably linked to the sequence encoding the APP polypeptide.

An aspect of the present invention provides methods to identify the products of cleavage at the β secretase cleavage site, which indicates, inter alia, the relative liability of the modified β secretase substrate, may be done by a number of methods as described herein. In particular embodiments, such methods are various assays based on immunological detection by specific polyclonal or monoclonal antibodies and, alternatively, the use of peptide aptamers or single-chain monoclonal antibodies (which may be identified using phage display technologies). For instance, in particular embodiments such immunological reagents are and can be identified which specifically bind to either the novel carboxyl terminal or amino terminal epitopes at the end of the processed amyloid β-protein products, where such terminal epitopes are generated by β secretase cleavage of any of the modified β secretase substrates of the present invention.

In particular embodiments of the present invention, in addition to having changes at the β secretase cleavage site, the modified β secretase substrates may be engineered to have several further changes from wild-type APP. Among such further changes include changing amino acids in the Aβ peptide to match the human form of the peptide, the inclusion of one or more epitope tags, a K612V α-secretase inhibitory change, the inclusion of Familial Alzheimers' Disease associated mutations at the α or γ secretase cleavage sites and N-terminal or C-terminal peptide extensions.

An aspect of the present invention is a non-human transgenic animal expressing an endogenous APP gene modified by a knock-in mutation resulting in NF and EV flanking the beta-secretase cleavage site. The endogenous gene is expressed by it's native promoter in a normal spatial and temporal expression pattern. In particular embodiments, the endogenous gene is also modified to produce a protein wherein the alpha beta portion of the APP has the amino acid sequence of human alpha beta. In particular embodiments, the endogenous gene is also modified to produce a protein wherein the balance of the protein has the amino acid sequence of human APP. In further embodiments, the endogenous APP contains additional mutations correlated to disease states when present in human APP. Particular additional modifications of the APP gene include modifications at the gamma secretase cleavage site and at the alpha secretase cleavage site. In particular embodiments, the transgenic animals exhibit phenotypes including elevated beta secretase cleavage of APP, an increase in the ratio of beta-secretase to alpha secretase cleavage of APP and/or elevated production of beta amyloid. In particular embodiments, the beta amyloid is soluble beta amyloid.

An aspect of the present invention is a transgenic non-human animal harboring multiple transgenes. In particular embodiments, the transgenic animal expressing an APP polypeptide having the NFEV (SEQ ID NO: 4) β secretase cleavage site also carry at least one additional transgene directing expression of a protein associated with Alzheimer's Disease. Additional genes may be a presenilin 1, tau, α-synuclein and β secretase gene. In further embodiments, the additional genes may be further combined to produce multiply transgenic animals.

These and other aspects of the invention will be apparent to those of skill in the art

BRIEF DESCRIPTION OF THE DRAWINGS

FIG. 1. Western Blot analysis of NFEV KI heterozygotes compared to wild type litter mates after G2-10 immunoprecipitation of DEA brain extracts. The blots were probed with antibody A. 6E10, which recognizes the three humanizing mutations and B. G2-10, which recognizes both murine and humanized Aβ at the Aβ40 neo-epitope, thus indicating the elevated levels seen in the heterozygotes compared to wild type litter mates. Aβ and EV amyloid standards are seen in the leftmost 8 lanes on the blot.

DETAILED DESCRIPTION OF THE INVENTION

Figure 2A:
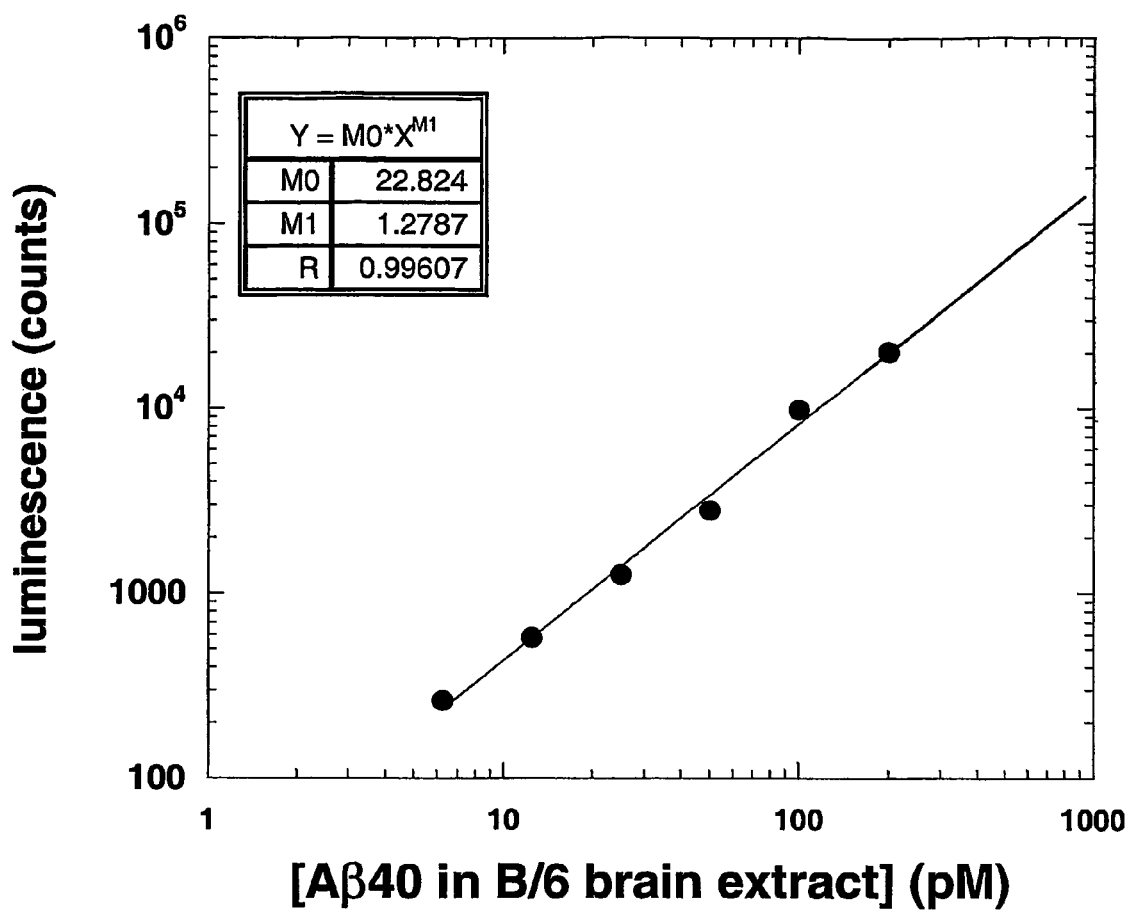
FIG. 2. Sandwich ELISA analysis of NFEV KI heterozygous mice compared to wild type litter mates and APP-YAC mice. A. The standard curve power law fit to six standards assayed in a wild type C57B1/6 mouse brain extract. B. Direct comparison of amyloid levels measured in a 6E10/G2-10 sandwich ELISA for NFEV KI heterozygotes, wild type litter mates and APP-YAC mice. These data indicate an approximately eight fold enhancement of processing of the NFEV substrate in a 2 month old animal compared to a human wild-type APP-YAC mouse roughly five times older.

The present invention provides non-human transgenic animals having an amyloid precursor protein wherein the amino acids flanking the β secretase cleavage site are NF and EV. The transgenic animals are useful to determine whether candidate compounds can alter the in vivo rate of cleavage of an amyloid precursor protein by β secretase. In particular embodiments, the amyloid precursor protein is further modified so that it encodes a human form of the Aβ peptide or of the entire APP protein. Further, the amyloid precursor protein can be modified, at sites other than the β secretase site, to include one or more mutations associated with Alzheimer's Disease. Additionally, the transgenic animals can carry additional genes having mutations associated with Alzheimer's Disease, particularly mutant forms of such genes that are associated with Familial Alzheimer's Disease, including mutations that alter the rate of cleavage at the α or γ secretase cleavage sites. Tissues and cell lines derived from these animals are also provided. Finally, the invention provides methods of screening candidate compounds to determine the effect of the compounds on the cleavage of amyloid precursor protein by β secretase.

An important feature of the present invention is that it provides a non-human transgenic animal model exhibiting an elevated in vivo rate of cleavage at the β secretase site. Because the rate of cleavage at the β secretase site is elevated the animal model provides a system which facilitates analysis of products produced by cleavage at both the β secretase cleavage site and a second cleavage at the α or γ secretase cleavage sites. Therefore, the animal model is also useful for determining whether compounds alter the in vivo rate of cleavage at the α or γ secretase cleavage sites. An important aspect of this invention is that the animal model provided herein allows these determinations to be made both in the presence or absence of phenotypic expression of other aspects of Alzheimer's Disease pathology.

Transgenic Animals

A variety of vectors useful for the construction of transgenic animals are well known and used in the art The choice of vector is often dependent on the targeting strategy, whether genetic regulatory elements will be required to express the encoded protein and the selection strategy. As used herein, a "transgenic" animal means any non-human animal having one of the various forms of genetic alterations used in the art including application of gene-targeting by homologous recombination at defined locations in the genome, random integration, so-called knock-in (KI), knock-out (KO), or alternatively transgenes [plasmids, YACs, BACs] incorporated at various locations in the genome. In the present invention, it is preferred, but not required, that the genetic alterations are introduced into the animal's endogenous APP gene using a gene-targeting approach via homologous recombination knock-in strategy. In instances where it is desirable to construct a vector for independent expression of a modified APP gene inserted into the genome at another location, promoter elements operably linked to the coding sequence should be included. It is preferred that such elements are neural or neuronal specific promoters. However, other promoters can be used to direct expression of the protein in either selected or in all tissue types.

The methods used for generating transgenic mice are well known to one of skill in the art. See "Manipulating the Mouse Embryo" by Brigid Hogan et al. (Ed. Cold Spring Harbor Laboratory) 1986, and Leder and Stewart, U.S. Pat. No. 4,736,866 for exemplary methods for the production of a transgenic mouse.

It is possible to carry out the genetic transformation of a zygote (and the embryo and mature organism which result therefrom) by the placing or insertion of exogenous genetic material into the nucleus of the zygote or to any nucleic genetic material which ultimately forms a part of the nucleus of the zygote. The genotype of the zygote and the organism which results from a zygote will include in a heritable fashion the exogenous genetic material. Additionally, the inclusion of exogenous genetic material in the zygote will result in a phenotype expression of the exogenous genetic material. The genotype of the exogenous genetic material is observable upon the cellular division of the zygote. However, the phenotype expression, e.g., the production of a protein product or products of the exogenous genetic material; or alterations of the zygote's or organism's natural phenotype, will occur at that point of the zygote's or organism's development during which the particular exogenous genetic material is active.

The genetic transformation of various types of organisms is disclosed and described in detail in U.S. Pat. No. 4,873,191, issued Oct. 10, 1989, which is incorporated herein by reference to disclose methods of producing transgenic organisms. The genetic transformation of organisms can be used as an in vivo analysis of gene expression during differentiation and in the elimination or diminution of genetic diseases by either gene therapy or by using a transgenic non-human mamma as a model system of a human disease. This model system can be used to test putative drugs for their potential therapeutic value in humans.

The exogenous genetic material can be placed in the nucleus of a mature egg. It is preferred that the egg be in a fertilized or activated (by parthenogenesis) state. After the addition of the exogenous genetic material, a complementary haploid set of chromosomes (e.g., a sperm cell or polar body) is added to enable the formation of a zygote [fusion of the pronuclei]. The zygote is allowed to develop into an organism such as by implanting it in a recipient pseudopregnant female. The resulting organism is analyzed for the integration of the exogenous genetic material. If positive integration is determined, the organism can be used for the in vivo analysis of the gene expression and phenotypic consequences, aspects of the phenotype may be related to or model particular genetic diseases. Studies of a number of different types of genetic diseases have been performed utilizing such transgenic animals. Studies relating to Alzheimer's disease are disclosed within published PCT application WO89/06689 and PCT application WO89/06693, both published on Jul. 27, 1989, disclose genetic sequences related to Alzheimer's Disease and the incorporation of such sequences into the genome of transgenic animals.

Embryonic target cells at various developmental stages can be used to introduce transgenes. Different methods are used depending on the stage of development of the embryonic target cell. The zygote traditionally is usually best established target for micro-injection. In the mouse, the male pronucleus reaches the size of approximately 20 micrometers in diameter which allows reproducible injection of 1-2 pl of DNA solution. The use of zygotes as a target for gene transfer has an advantage in that in most cases the injected DNA will be incorporated into the host gene before the first cleavage (Brinster, et al. (1985) Proc. Natl. Acad. Sci. U.S.A. 82, 4438-4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Viral infection can also be used to introduce transgene into a non-human animal. The developing non-human embryo can be cultured in vitro to the blastocyst stage. During this time, the blastomeres can be targets for retroviral infection (Jaenich, R. (1976) Proc. Natl. Acad. Sci U.S.A. 73, 1260-1264). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retrovirus carrying the transgene (Jahner, et al. (1985) Proc. Natl. Acad. Sci. U.S.A. 82, 6927-6931; Van der Putten, et al. (1985) Proc. Natl. Acad. Sci U.S.A. 82, 6148-6152). Transfection is easily and efficiently obtained by culturing the blastomeres on a monolayer of virus-producing cells (Van der Putten, supra; Stewart, et al. (1987) EMBO J. 6, 383-388). Alternatively, infection can be performed at a later stage. Virus or virus-producing cells can be injected into the blastocoele (Jahner, D., et al. (1982) Nature 298, 623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner, D. et al. (1982) supra) or lentiviral delivery (Porteus and Baltimore, 2003, Science 300 (5620):763).

A third type of target cell for transgene introduction is the embryonal stem cell (ES). ES cells are obtained from pre-implantation embryos cultured in vitro and fused with embryos (Evans, M. J., et al. (1981) Nature 292, 154-156; Bradley, M. O., et al. (1984) Nature 309, 255-258; Gossler, et al. (1986) Proc. Natl. Acad. Sci U.S.A. 83, 9065-9069; and Robertson, et al. (1986) Nature 322, 445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240, 1468-1474.

Once a transgenic animal has been created, it is a routine matter to cross-breed the animal with other transgenic animals to produce multi-genic animal models, i.e., animal models carrying multiple transgenes or genetic alterations. In this manner one can create animal model systems in which the effects or interactions of multiple transgenes can be studied. Such animals, and the tissues and cell lines derived therefrom, can be utilized in screens for drugs that affect the pathways in which the transgenes are involved. For example, the transgenic animal of the present invention can be bred with animals transgenic for one or more genes implicated in Alzheimer's Disease including tau, presenilin, β secretase and synuclein. The second gene can be a human, humanized or animal form of the gene. The gene can be wild-type, a knocked-out gene, or carry a mutation associated with Alzheimer's Disease. In a particular embodiment of the invention, a bi-genic animal possesses the altered β secretase site described herein and a knock-out of the animal's β secretase gene. In another embodiment, a bi-genic animal transgenic for the modified β secretase site also carries a human or humanized β secretase gene. In another embodiment, a bi-genic animal transgenic for the modified β secretase site also carries a human, humanized or mutant presenilin-1 gene. In further embodiments, bi-genic animals are crossed with transgenic animals to introduce a third transgene associated with Alzheimer's Disease, which gene can be human or humanized. Using such techniques, one can create particular metabolic pathways for the processing of amyloid precursor protein in the transgenic animal. Of particular importance is that one can create a non-human animals in which most or all of the important proteins and enzymes involved in processing APP are expressed from transgenes in a human or humanized form.

Multi-genic animals have the same utility as the transgenic animal carrying an amyloid precursor protein with the NFEV β secretase cleavage site, but can have additional utilities based on the additional transgenes. Multi-genic animals can be used to screen for drugs that, for example, affect the rate of processing of amyloid precursor protein to produce Aβ peptide in the presence of one or more additional transgenes.

Animals of the present invention can have changes in the amyloid precursor protein in addition to the alteration of the β secretase cleavage site to NFEV (SEQ ID NO: 4). For example, further changes can be introduced to humanize the amyloid precursor protein by changing the codons of the animal's native amyloid precusor protein to match those of the human protein. The humanization can be limited to the region of the Aβ peptide, the α secretase or γ secretase cleavage sites, or may humanize other portions of the amyloid precursor protein. Alternatively, a human amyloid precursor protein can be modified to NFEV (SEQ ID NO: 4) at the β secretase cleavage site and introduced into an animal. The animal can lack a functional amyloid precursor protein gene (e.g., a knock out) or the human gene can be knocked-in to replace the animals' native gene. However, because cleavage at the modified β secretase cleavage site yields particular termini which can be specifically detected, one may prefer to leave the native amyloid precursor protein gene intact. In additional embodiments, the amyloid precusor protein can be changed to introduce Alzheimer's Disease associated mutations at other sites in the protein. Examples of such mutations are Alzheimer's Disease associated mutations in the regions of the α secretase cleavage site and the γ secretase cleavage site. Such animals are useful in screening for compounds that affect the rate of production of Aβ peptide when multiple mutations are present in the amyloid precursor protein. As described above, animals transgenic for multiple changes in their amyloid precursor protein can be crossed with transgenic animals that carry other Alzheimer's associated genes including presenilin, tau and synuclein, to produce multi-genic animals.

Amyloid Precursor Protein

The amyloid precursor protein in the transgenic animals of the present invention carries a modified β secretase cleavage site where the sequence has been changed to NFEV (SEQ ID NO: 4). Except where indicated, the numbering of the amino acids in APP used herein is based on the 695 amino acid version of APP described in Kang et al., 1987, Nature 325: 733-736. There are two other major versions of APP, having 751 amino acids and 770 amino acids (see Ponte et al., 1988, Nature 331:525-527 for the 751 amino acid version and Kitaguchi et al., 1988, Nature 331:530-532 for the 770 amino acid version). One skilled in the art will understand how to translate the numbering used herein, based on the 695 amino acid version of APP, into the corresponding numbering for other versions of APP. For example, the transgenic animals of the present invention carry an amyloid precursor protein with a modified β secretase cleavage site where the first amino acid of the cleavage site sequence is changed K612V, based on the numbering of the 695 amino acid version. This change would correspond to a K668V mutation in the 751 amino acid version and a K687V mutation in the 770 amino acid version.

Further to the point of modifications of any of these three amino acid versions of APP, all of the following modifications are also considered to fall within the definition of an amyloid precursor protein having the modified β secretase cleavage site of NFEV (SEQ ID NO: 4). It is known that full length APP is encoded by a gene that is naturally differentially spliced to result in the three amino acid variants, or isoforms, of the protein: 695, 751, and 770 amino acids in length. A recombinant APP protein can be generated by subcloning the cDNA encoding the APP isoform of interest in an expression vector containing appropriate promoters and stop signals. This vector containing the APP cDNA can then be expressed in a variety of organisms to generate the APP protein. By manipulating the cDNA subcloned into the expression vector, modified APP proteins can be recombinantly generated. Using commonly applied assays measuring Aβ peptide production, it can be determined if the newly modified APP protein is a substrate of β secretase. For example, in this invention, the APP protein is modified by altering the amino acids surrounding the β secretase cleavage site from KMDA (SEQ ID NO: 6) to NFEV (SEQ ID NO: 4). This modified APP was verified as a substrate for β secretase in a cellular assay. If insertion, deletion, or alteration of codons into the cDNA of the modified APP protein resulted in an APP protein that could still be cleaved by β secretase, then the newly modified APP would still be a β secretase substrate and useful in a transgenic animal of this invention. For example, by using restriction enzymes, PCR, or linker insertion/replacement to manipulate the modified APP cDNA, portions of the 5'end of the gene can be specifically deleted in-frame. These deletions can be as small as 3 nucleotides, resulting in the removal of a single amino acid, and they can be as large as 1782 nucleotides in the modified $APP_{695}$ gene, resulting in the removal of the entire N-terminus of the protein up to the modified β secretase cleavage site. Although the removal of the entire N-terminus is an extreme example, the removal of 30 codons to delete 10 amino acids or 300 nucleotides, resulting in the deletion of 100 amino acids, can result in fully functional β secretase substrates. These newly derived modified APP proteins can all then be tested in the cellular system described to determine if they remain substrates of β secretase. Similarly, molecular manipulations can be done downstream of the β secretase cleavage site which might delete anywhere from 3 to 291 nucleotides. This would result in the deletion of anywhere from 1 to 97 amino acids downstream of the modified β secretase cleavage site. In the case of deleting amino acids downstream of the β secretase cleavage site, the deletion does not necessarily have to remain in-frame. An in-frame deletion of codons will result in a protein that has specific amino acids removed. A deletion of nucleotides that does not remain in-frame will result in a truncated protein. Again, in either the in-frame or the out-of-frame deletion, the resulting modified APP can be tested in the assay described to determine if the newly modified APP is a substrate of β secretase.

Alternately, insertion of amino acids into APP with the modified β secretase cleavage site can be done using standard molecular biology techniques, such as linker/fragment insertion and PCR. After expression in an appropriate recombinant host, these manipulations will result in APP proteins that have been altered from the original modified APP. Insertions as small as 3 nucleotides will be tolerated by the host of the recombinant vector and can be made in-frame upstream and/or downstream of the modified β secretase cleavage site. These modified APP genes can be tested in the cellular system described to determine if the newly modified APP protein is a substrate of β secretase and therefore useful in a transgenic animal of this invention.

Finally, by using standard molecular biology techniques, any number of amino acids in the modified APP protein can be altered without changing the absolute number of amino acids in the protein. For example: the codon GTT encodes the amino acid valine. If this is altered by site directed mutagenesis to ATT, the codon would then encode the amino acid isoleucine. Although this is a relatively conservative change, the codon could also have been altered to AAT, which encodes asparagine, a non-conservative change. In any given protein, from one to multiple amino acid changes can be made in a similar manner. Depending on the location of the amino acid changes, the altered APP protein may or may not retain function as a substrate for β secretase. The recombinant protein(s) generated from the altered APP cDNA(s) can be checked using standard assays for the measurement of the production of Aβ peptide.

Thus, any of the above described deletions, insertions, and amino acid alterations made to an APP protein having NFEV (SEQ ID NO: 4) at the β secretase cleavage site that result in a biologically active protein that is cleaved by β secretase is useful as described herein. Basic molecular biology techniques to achieve such deletions, insertions, and amino acid alterations can be found in references such as the following: Ausubel, F. M., R. Brent, et al., Eds. (1992). Short Protocols in Molecular Biology: A compendium of methods from Current Protocols in Molecular Biology. Current Protocols in Molecular Biology. New York, N.Y., Green Publishing Associates and John Wiley & Sons; Berger, S. L. and A. R. Kimmel, Eds. (1987); Guide to Molecular Cloning Techniques. Methods in Enzymology. Orlando, Fla., Academic Press, Inc.; and Innis, M. A., D. H. Gelfand, et al., Eds. (1990). PCR Protocols: A Guide to Methods and Applications. San Diego, Calif., Academic Press, Inc.

Various constructs useful in generating animals of the present invention can be made by use of the polymerase chain reaction (PCR) to amplify desired portions of DNA encoding APP and other DNA sequences, which can be then be cloned into expression and/or targeting vectors by methods well known in the art. Primers for PCR will generally include a small part of the DNA sequence it is desired to amplify as well as convenient cloning sites and/or linker peptide sequences. The PCR primers can be used to amplify the desired sequences from sources such as previously cloned DNA sequences, cDNA libraries, or genomic libraries. The amplified sequences can be cloned into suitable expression vectors. Methods of PCR and cloning are well known in the art and can be found in standard reference materials such as those listed below.

Standard techniques for cloning, DNA isolation, amplification and purification, for enzymatic reactions involving DNA ligase, DNA polymerase, restriction endonucleases and the like, and various separation techniques are known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth. Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) Practical Methods in Molecular Biology; Glover (ed.) (1985) DNA Cloning Vol. I and II, IRL Press, Oxford, UK; Hames and Higgins (eds.) (1985) Nucleic Acid Hybridization, IRL Press, Oxford, UK; Setlow and Hollaender (1979) Genetic Engineering: Principles and Methods, Vols. 1-4, Plenum Press, New York, and Ausubel et al. (1992) Current Protocols in Molecular Biology, Greene/Wiley, New York, N.Y., Kornberg & Baker DNA Replication, W.H. Freeman, NY, $2^{nd}$ Ed., (1992).

PCR reactions can be carried out with a variety of thermostable enzymes including but not limited to AmpliTaq, AmpliTaq Gold, or Vent polymerase. For AmpliTaq, reactions can be carried out in 10 mM Tris-Cl, pH 8.3, 2.0 mM $MgCl_2$, 200 μM of each dNTP, 50 mM KCl, 0.2 μM of each primer, 10 ng of DNA template, 0.05 units/μl of AmpliTaq. The reactions are heated at 95° C. for 3 minutes and then cycled 35 times using suitable cycling parameters, including, but not limited to, 95° C., 20 seconds, 62° C., 20 seconds, 72° C., 3 minutes. In addition to these conditions, a variety of suitable PCR protocols can be found in PCR Primer, A Laboratory Manual, edited by C. W. Dieffenbach and G. S. Dveksler, 1995, Cold Spring Harbor Laboratory Press; or PCR Protocols: A Guide to Methods and Applications, Michael et al., eds., 1990, Academic Press.

It is desirable to sequence the DNA encoding the APP having a modified β secretase site, or at least the junction regions of the various portions of the polypeptides in order to verify that the desired portions have in fact been obtained, joined properly, and that no unexpected changes have been introduced into the sequences by the PCR reactions.

Assays

A variety of immunoassay formats may be used to select antibodies specifically immunoreactive with a particular protein, polypeptide, or peptide. For example, solid-phase ELISA immunoassays are routinely used to select monoclonal antibodies specifically immunoreactive with a protein, polypeptide, or peptide. See Harlow & Lane, 1988, Antibodies, A Laboratory Manual, Cold Spring Harbor Publications, New York, for a description of immunoassay formats and conditions that can be used to determine specific immunoreactivity. In assays of the present invention, antibodies that specifically recognize the neo-epitopes created by β secretase cleavage of APP at the modified NF EV (SEQ ID NO: 4) site are particularly useful.

In assays of the present invention one is generally measuring the production of Aβ peptide from amyloid precursor protein. However, one can measure a variety of cleavage products including polypeptides produced from the cleavage of the β secretase site including "sAPPβ fragment", an approximately 100 kD amino terminal fragment produced when APP is cleaved by β secretase. The C-terminal fragment produced after cleavage of the β secretase site without cleavage at the α or γ secretase site can also be measured, especially in model animals lacking the relevant secretase. Alternatively, animals of the present invention provide a system in which α secretase cleavage is elevated, thereby enhancing ones' ability to measure peptide production via cleavage at the γ secretase site. Thus, measuring β secretase activity can be performed by measuring a variety of endpoints (Aβ peptide production, sAPPβ production, c-Terminal fragment production, behavioral, brain electrical activity, PET, etc.) and using a myriad of measurement modalities.

The present invention provides a method of identifying a compound that inhibits β secretase comprising:

(a) providing a transgenic non-human animal which expresses an amyloid precursor protein polypeptide comprising a β secretase cleavage site of NFEV (SEQ ID NO: 4), (b) measuring the level of β secretase activity on the polypeptide in the animal, a cell line derived therefrom or in a tissue sample, in the absence of the compound, (c) exposing animal, a cell line derived therefrom or tissue sample to the substance and measuring the level of β secretase activity in the presence of the substance, where a decrease in the level of β secretase activity in the presence as compared to the absence of the compound indicates that the substance inhibits β secretase.

Moreover, the present invention also provides a method of identifying a compound that inhibits Aβ production through various mechanisms other than beta-secretase cleavage. For instance, one can envision using animals of the present invention to screen for inhibitors of γsecretase, agonists of α-secretase, compounds that affect the signaling pathways that alter the production and/or clearance of Aβ. Since all of these various mechanisms could be investigated and compounds identified by measuring changes in Aβ production, the animals of the present invention prove more useful than just to identify inhibitors of β-secretase.

In particular, the present invention also provides a method of identifying a compound that inhibits Aβ production comprising:

(a) providing a transgenic non-human animal which expresses an amyloid precursor protein polypeptide comprising a β secretase cleavage site of NFEV (SEQ ID NO: 4), (b) measuring the level of Aβ production in the animal, a cell line derived therefrom or in a tissue sample, in the absence of the compound, (c) exposing animal, a cell line derived therefrom or tissue sample to the substance and measuring the level of A, produced in the presence of the substance, where a decrease in the level of Aβ producted in the presence as compared to the absence of the compound indicates that the substance inhibits Aβ production.

The manner in which the level of β secretase activity is measured will be determined by the nature of the polypeptide and, often, the characteristics of the animal, cell line or tissue. A variety of techniques are available including assay employing antibodies that detect specific cleavage products of amyloid precursor protein. However, other techniques can be employed for the study of Aβ peptide production in vivo and in tissue samples including microcomputer x-ray tomography, positron emission techniques including SPECT (Single position emission computer tomography) and PET tracer, multi-photon microscopy and other non-invasive imaging modalities. Behavioral assessments and in vivo electrical activity measurements are also useful means of studying animals.

A particularly useful aspect of the modified β secretase cleavage site is generation of unique neo-epitopes after cleavage at the site. The sAPPβ fragment has a unique C-terminus ending in NF. Further, the C-terminal fragment and the Aβ peptide produced have a unique N-terminus ending in EV. Employing specific polyclonal or monoclonal antibodies, one can specifically detect these cleavage products even in the presence of products of the animals' endogenous, wild-type amyloid precursor protein. Moreover, if the amino acid sequence of the Aβ peptide is humanized, antibodies can be used to specifically detect the humanized form of the peptide even in the presence of the animals' endogenous wild-type peptide. Thus one can employ commonly used techniques of antibody generation and assay formats to specifically detect the products of the polypeptide encoded by the particular transgene employed.

One skilled in the art would recognize that what is sought in terms of "a decrease in the level of β secretase activity in the presence as compared to the absence of the substance" is a non-trivial decrease. For example, if in the assays described herein there is found a 1% decrease, this would not indicate that the substance is an inhibitor of β secretase. Rather, one skilled in the art would attribute such a small decrease to normal experimental variation. What is looked for is a significant decrease. For the purposes of this invention, a significant decrease fulfills the usual requirements for a statistically valid measurement of a biological signal. For example, depending upon the details of the embodiment of the invention, a significant decrease might be a decrease of at least 10%, preferably at least 20%, more preferably at least 50%, and most preferably at least 90%, depending of course on the variability, statistical power, effect size and least significant sample size N.

When β secretase activity is measured by monitoring the production of Aβ, it will usually be desirable to further test inhibitors that are identified by the methods of the present invention to determine that such inhibitors actually act at the step of β secretase activity rather than at some other step in APP processing. Assays that are known to be specific for the various steps of APP processing can be used for this purpose. For example, the assay of Karlström et al., (Journal of Biological Chemistry, published on Dec. 13, 2001 as Manuscript C100649200) is only capable of detecting inhibitors of γ secretase and cannot also detect inhibitors of other steps of APP processing such as, e.g., inhibitors of β secretase. If an inhibitor identified by the methods of the present invention is found to also be an inhibitor when tested in the assay of Karlström et al., then that inhibitor is at least a γ secretase inhibitor. It is still possible that that inhibitor could be a β secretase inhibitor as well. Further tests known in the art can determine this.

Although a wide variety of substances can be screened by the methods of the present invention, preferred substances for screening are libraries of low molecular weight organic compounds. Low molecular weight organic compounds are preferred because they are more readily absorbed after oral administration, have fewer potential antigenic determinants, and are more likely to cross the blood/brain barrier than larger molecules such as nucleic acids or proteins.

Once identified by the methods of the present invention, the low molecular weight organic compounds may then be produced in quantities sufficient for pharmaceutical testing and formulated in a pharmaceutically acceptable carrier (see, e.g., Remington's Pharmaceutical Sciences, Gennaro, A., ed., Mack Publishing, 1990, for suitable methods). The low molecular weight organic compounds may be administered to cell lines relevant to Alzheimer's disease, animal models of Alzheimer's disease, or Alzheimer's disease patients.

The methods of the present invention can be used to screen libraries of substances or other sources of substances to identify substances that are inhibitors of β secretase. Such identified inhibitory substances can serve as "leads" for the development of pharmaceuticals that can be used to treat patients having Alzheimer's disease or in a prophylactic manner to prevent or delay the development of Alzheimer's disease. Such leads can be further developed into pharmaceuticals by, for example, subjecting the leads to sequential modifications, molecular modeling, and other routine procedures employed in the pharmaceutical industry. The β secretase inhibitors identified by the present invention may also be tested in animal models of Alzheimer's disease such as the various transgenic mouse models that are known in the art.

The conditions under which substances are employed in the methods described herein are conditions that are typically used in the art for the study of protein-ligand interactions or enzyme inhibition studies. When testing compounds in tissue samples or cell lines derived from the animals of this invention one can typically use routine conditions as practiced in the art: e.g., salt conditions such as those represented by such commonly used buffers as PBS or in tissue culture media; a temperature of about 4° C. to about 55° C.; incubation times of from several seconds to several hours or even up to 24 or 48 hours. A variety of reagents may be present, e.g., ATP, ATP analogs, salts, buffers, neutral proteins such as albumin, detergents, protease inhibitors, nuclease inhibitors, antimicrobial agents, etc. Screening for the identification of enzyme-specific inhibitors is a well-known procedure in the pharmaceutical arts and numerous conditions under which such screening has been done are available in the literature to guide the practitioner of the present invention.

The following Examples are provided for further illustration of the invention and are not meant to be limiting upon the scope of the appended claims.

EXAMPLE 1

The Modified β Secretase Cleavage Site is a Substrate for β Secretase

The relative suitability of amyloid precursor protein having a modified β secretase site of as a better substrate for β secretase than the wild type KMDA (SEQ ID NO: 6) cleavage site was assessed. Plasmid DNA constructs were made for expressing an $APP_{695}$-derived polypeptide with the wild type KMDA (SEQ ID NO: 6) and modified NFEV (SEQ ID NO: 4) β secretase cleavage sites, respectively, in HEK293T cells. A plasmid carrying the β secretase site mutation known as the Swedish mutation, NLDA, was also constructed. The plasmids were prepared using standard recombinant methods and used to transfect HEK293T cells.

Transient transfection was performed using LipofectaminePlus reagent (Gibco/BRL, Rockville, Md.) according to the instructions of the manufacturer. Media was harvested 48 hrs post transfection. Western blot analysis of the polypeptides produced and processed by endogenous β and γ secretases was used to determine levels of sAPP. IP/Western blots were performed to determine levels of Aβ peptide. Several volumes of conditioned media, 20 μl, 10 μl, 5 μl, 2.5 μl, from the transiently transfected cells were analyzed on 10% SDS-PAGE gels and transferred to PVDF for the measurement of sAPP. Each blot contained a titration of conditioned media from the wild type APP transfected cells to normalize for any experimental variations derived from transferring of the gels and western blot detection. The blots were probed with antibody LN27 (Zymed, California) to detect the secreted APP, sAPP. The relative amount of total APP expressed in each transfection was determined by scanning densitometry of each western blot.

To determine the levels of Aβ, each of the conditioned media were immuno-precipitated and analyzed via the following method. 5 μg of monoclonal antibody G2-10 (a monoclonal antibody that immunologically binds to the carboxyl end of Aβ40, obtained from University of Heidelberg) was added to 1 ml of each conditioned media. The mixture was rotated overnight at 4° C. for 16 hours. 25 μL of a 50% slurry of Protein A sepharose Fast flow beads (Amersham, N.J.) was added and incubation continued, rotating, for 2 hours at 4° C. The beads were pelleted and the supernatant was removed. The beads were washed once with 1 ml PBS. This material was then run on SDS-Tricine gels for analysis. 20 μl of 2× tricine loading buffer was added to the pellet and the mixture was heated at 95° C. for 5 minutes. A pipette tip was used to mix and load the whole mixture (beads included) onto a Bio-Rad 10-20% Tricine gel. The gels were electrophoresed at 125 Volts for 2 hours and 15 minutes and then transferred onto 0.2 μm nitrocellulose backed by a 0.1 μm nitrocellulose membrane for 75 minutes at 100V constant. Blots were then washed in PBS and boiled in PBS for 5 minutes before blocking in PBS plus 0.05% Tween-20 (PBST) with 5% non-fat milk for 60 minutes at room temperature. The milk was washed off twice with PBST and the blots were incubated overnight at 4° C. with G2-10 in PBST (1:1000 dilution). Blots were washed five times for 5 minutes each with large volumes of PBST. The secondary antibody, Goat anti-mouse IgG2b-HRP (Southern Biotechnology Associates, Inc., Birmingham, Ala.), was added at 1:5000 in PBST-5% milk and the blots were incubated, rocking, for 1 hour at room temperature. The blots were again washed, five times for 10 minutes each in large volumes of PBST. The substrate Pico ECL (Pierce) was added for 5 minutes and the blots were exposed to Kodak BioMax film. After western analysis was complete, the bands were quantitated by densitometry. For both the sAPP and the Aβ, the GFP control plasmid transfection serves as the background reference level (1×).

The effect of the β secretase cleavage site sequence on Aβ production in cells was assessed. Expression of $APP_{695}$-derived polypeptide having the modified sequence, NFEV (SEQ ID NO: 4), resulted in the production of high levels of Aβ. The levels of Aβ were comparable to the levels produced upon expression of $APP_{695}$-derived polypeptide carrying the Swedish mutant NLDA (SEQ ID NO: 7) at the β secretase cleavage site. Expression of these two $APP_{695}$-derived polypeptides resulted in approximately fifteen to twenty fold higher levels of Aβ than $APP_{695}$-derived polypeptide having the wild-type KMDA (SEQ ID NO: 6) sequence at the β secretase cleavage site.

When APP-derived polypeptides comprising modified β secretase cleavage site sequence NFEV was transfected into immortalized β secretase −/− mouse fibroblast cells (obtained from Johns Hopkins University), no production of Aβ was observed. Production of Aβ in β secretase −/− cells could be rescued by co-transfection of the APP-derived polypeptides having the modified cleavage site with a human β secretase gene. These data demonstrate that β secretase is responsible for the cleavage of the modified β secretase cleavage site sequence.

EXAMPLE 2

Generation of NFEV-APP Knock-In (KI) Mice

Construction of Knock-in Targeting Vector pAPP-KI-TK

A search of the NCBI mouse genome sequence data base with a mouse App cDNA sequence (NM-007471) identified a bacterial artificial clone (BAC; clone ID RP23-99P18) containing mouse App of 129SvEV genetic background, from which a 6.8 kilobase (kb) Kpn I fragment containing App exons 16 and 17 was subcloned. The modification of the endogenous β secretase cleavage site, from KMDA (SEQ ID NO: 6) to NFEV (SEQ ID NO: 4), and three other residues within the Aβ region (humanizing modifications $Gly_5$, $Phe_{10}$ and $Arg_{13}$ to Arg, Tyr and His, respectively) was performed by site-directed mutagenesis (Stratagene, California, USA) using a single mutagenizing primer:

5'-GAAGAGATCTCGGAAGTGAACTTC-GAAGTGGAATTCCGA

CATGATTCAGGATATGAAGTCCATCAT-CAAAAACTGGTAGG-3' (SEQ ID NO: 8).

A PGK-Neo cassette flanked by a lox P site on either side was inserted into a unique BamH I site in intron 16. A Herpes simplex virus thymidine kinase (TK) gene was inserted between the end of the App genomic sequence and the vector sequence, to complete the construction of knock-in targeting vector pAPP-KI-TK.

ES Cell Transfection

V6.5 mouse ES cells (Eggan K, et al., *Proc. Natl. Acad. Sci. USA* 98, 6209-6214 (2001)) were cultured as described (Joyner, A. L. (Ed.) Gene targeting; a practical approach (Oxford University Press, New York, 2000)) in ES cell qualified DMEM with 15% FBS containing 1,000 units/ml ESGRO on mitomycin C treated neomycin-resistant primary feeder fibroblasts (all ES cell culture reagents were from Cell & Molecular Technologies, New Jersey, USA). Electroporation was carried out using 20 μg of Not I-linearized pAPP-KI-TK targeting vector and approximately $6 \times 10^6$ ES cells as described (Id.). Selection for neomycin resistant and TK-negative colonies was carried out 30 h later and subsequently for 7 days with 250 μg/ml Geneticin (Invitrogen, California, USA) and 2 μM ganciclovir (Novagen, Wis., USA). ES colonies were picked and genomic DNA was isolated as described (Laird P W, et al., Nucleic Acids Res. 19, 4293 (1991)).

Targeted ES clones were identified by Southern-blot analysis of genomic DNA digested with Spe I using a 5' external probe (4 kb Kpn I fragment immediately 5' to the 6.8 kb Kpn I fragment that contains exons 16 and 17).

The wild-type and targeted alleles were identified as a 16 kb and a 9.2 kb fragment, respectively. Homologous recombination was further confirmed by a second Southern-blot analysis using Xho I digestion and an internal Neo gene fragment as the probe, in which wild-type and targeted alleles were identified as a 21 kb and a 7.2 kb fragment, respectively. The Neo probe was a 700 base pair fragment prepared by polymerase chain reaction:

forward primer: 5'-TTTTGACCCATATAGAACATGTCCC-3' (SEQ. ID NO: 9);

reverse primer: 5'-GCACATTAAATTCATGGCACCC-3' (SEQ ID NO: 10).

Of 1130 ES clones analyzed, 26 were identified and characterized as targeted carrying a single homologously recombined knock-in allele (2.2% targeting frequency). The presence of the modifications was confirmed by direct DNA sequencing of PCR products using primers flanking the AD coding region:

forward primer: 5'-CCTTTCCCTCCCTCCCCTTT-3' (SEQ ID NO: 11);

reverse primer: 5'-GGAAACTGGGACCACCTCTAA-3' (SEQ ID NO: 12).

Of the 26 targeted clones, 24 clones were confirmed to carry the desired modifications, and 3 ES clones were subsequently used in blastocyst microinjection to generate chimeras.

Microinjection and Animal Breeding

All animal protocols used herein were carried out under approved Animal Care and Use guidelines. ES cells were injected into C57BL/6 (Taconic Farms, N.Y., USA) host blastocysts to generate chimeras as described (Joyner, A. L. (Ed.) Gene targeting; a practical approach (Oxford University Press, New York, 2000)), which were subsequently crossed with C57BL/6 mice to derive mice bearing a germline-transmitted APP knock-in allele. Genomic DNA was isolated as described (Laird P W, et al., *Nucleic Acids Res.* 19, 4293 (1991)). Genotyping was carried out by both Southern-blot and PCR restriction enzyme analysis as described above. Additionally, tail DNA was sequenced using flanking primers to the knock-in mutation region of APP to confirm the Knock-in allele.

Mice heterozygous for the Knock-in allele were intercrossed. The homozygous knock-in progenies were genotypically confirmed. The sole presence of the gene-targeted allele as well as the absence of the endogenous mouse APP gene was determined by genomic southern and PCR analysis. Additionally, tail DNA was sequenced in the vicinity of the Knock-in mutations with flanking primers and confirmed all mutations in the homozygous mice.

EXAMPLE 3

IP/Western Blot Analysis of Heterozygous NFEV-hAPP KI mice vs. WT litter mates.

Heterozygous NFEV-hAPP KI mice were evaluated for the presence and functional targeting of the knock-in NFEV-hAPP protein by measuring the cleavage products of its proteolytic processing by endogenous β and γ secretase enzymes. Production of the EV form of the Amyloid 1-40 peptide, the result of β and γ secretase enzyme cleavages, was assayed after immuno-precipitation of mouse brain homogenates, followed by western blot analysis with various antibodies for immunoreactivity.

Antibodies

Mouse monoclonal antibodies WO-2, G2-10, and G2-11 were obtained from the University of Heidelberg (Ida et. al. Analysis of Heterogeneous BetaA4 Peptides in Human Cerebrospinal Fluid and Blood by a Newly Developed Sensitive Western Blot Assay. J Biol Chem 1996, 13; 271(37):22908-14). IgG was purified from hybridoma supernatant. Monoclonal antibody G2-10 recognizes the c-terminal 40 neo-epitope of either Aβ 1-40 or EV1-40, whereas mouse monoclonal G2-11 recognizes the c-terminal 42 neo-epitope of either Aβ 1-42 or EV1-42. Monoclonal antibody 6E-10, originally developed against amino acids 5-11 of human Aβ1-16 (Kim et. al. Production and characterization of monoclonal antibodies reactive to synthetic cerebrovascular amyloid peptide. Neuroscience Research Communications 1988, 2:121-130.), was purchased commercially (Signet, Cat# 9320-10). The 6E10 antibody does not recognize the murine form of Aβ since it differs from the human form at Aβ sites 5 and 10. A polyclonal anti-NF neo-epitope antibody was generated in rabbit (designated #2081) against the nSEVNF-c (SEQ ID NO: 13) peptide. This polyclonal antibody recognizes the cleaved NF-COOH terminus generated by β secretase proteolytic cleavage of NFEV-humanAPP protein. The rabbit sera was affinity purified using an SEVNF (SEQ ID NO: 13) affinity column and characterized with a biotinylated SEVNF (SEQ ID NO: 13) titration using standard sandwich immuno assay methods (*Antibodies, A Laboratory Manual*, Harlow and Lane, Cold Spring Harbor Laboratories, 1988.). Alkaline phosphatase (AP) was conjugated to both 6E10 and G2-10 using a commercial kit (Pierce, Cat#31493) according to the manufacture's instructions.

Mice

Mice produced from the chimeric mice described above were bred with wild type C57BL/6 mice. Germ-line transmission was confirmed by 3' and 5' southern analysis as well as restriction analyses of PCR products from tail DNA. Finally, the Aβ gene was cloned into a Topo Clone vector by flanking primers and sequenced. Two month old genotyped heterozygous mice were identified and separated from wild-type litter mates. Additionally, 10 month old homozygous mice expressing the wild type human APP gene on a yeast artificial chromosome were utilized for comparison in biochemical assays (Lamb et. al. Introduction and expression of the 400 kilobase amyloid precursor protein gene in transgenic mice. Nat Genet 1993 Sep.; 5(1):22-30).

Extraction of Soluble Amyloid 1-40 from Mouse Brain

Brains were harvested from each type of the three mice following $CO_2$ euthanasia and immediately frozen on dry ice. Brain hemispheres (typically 200-300 mg) were homogenized in extraction buffer in 10x volume to weight with a motorized homogenizer (IKA T8 Homogenizer, Fisher Scientific Cat# 14-259-74) at maximal speed for ~30 seconds. The extraction buffer contained 0.2% Diethylamine (Sigma, Cat# D-0806), 50 mM NaCl, and 1x complete Protease Inhibitor (Roche, Cat# 1836145). Samples were spun at 200,000 × G for 1 hour at 4° C., supernatants were removed and neutralized to pH of ~7.7 with 10% volume of 0.5M Tris HCl at pH of 6.8.

Immunoprecipitation

Immunoprecipitation was conducted immediately after neutralization by adding 10 ug of mouse monoclonal antibody G2-10 to 1000 uL of neutralized brain homogenate. 25 ul of a 75% slurry of Protein A beads (Amersham, cat# 17-0974-04) were immediately added and incubated overnight (16 hrs) at 4° C. The following morning, the slurry was spun at 1000×g, the supernatant removed and the bead pellet gently washed once time with 1 ml PBS to prepare for gel loading.

Western Blotting

The washed bead pellet was mixed with half volume of 3× Tricine loading buffer containing 10% β-mercaptoethanol and boiled for 5 minutes. 45 uL of each sample was then loaded onto a 10-20% Peptide gel (Bio-Rad, Cat# 345-0067) and run at 125 V for ~2 hrs. The eluted proteins were then transferred onto a 0.2 µm nitrocellulose membrane (Bio-Rad, Cat# 162-0232) backed by a 0.1 µm nitrocellulose membrane (Schleicher & Schuell Cat # 10402093) for 60 min at 380 mA constant current. The membranes were then washed in PBS, boiled for 5 min in PBS prior to blocking with blocking agent (LI-COR, LINCOLN, NE, Cat # 927-40000) for 60 min.

To detect the EV Amyloid 1-40, the blot was incubated with either 1:1000 6E10 mouse monoclonal antibody or 1:1000 G2-10 mouse monoclonal antibody overnight at 4° C. The blots were washed and incubated with a secondary goat anti-mouse IgG1 antibody conjugated with a 800 nm IRDye (Rockland Immunochemicals, Cat# 610-132-121) for 6E10 and a custom (Code CUST54) 800 nm IRDye IgG2b for G2-10, both at 1:2500 dilution in Licor block (0.1% Tween) for 1 hour. Blots were then again washed 5× with PBS (0.1% Tween) and scanned on a LI-COR ODESSEY Infra-red scanner (LICOR, LINCOLN, NE). Fluorescence intensities were measured and quantification of amyloid 1-40 was completed.

The western blot shows four lanes of Aβ1-40 peptide standards as well as four lanes of EV 1-40 standards (FIG. 1). In the last four lanes to the right, alternating wild type litter mates (WT) and heterozygous (HET) mice brain homogenates were run. Upper blot A was probed with antibody 6E10. The bright bands in the heterozygous lanes confirm the integration of the Knock-In construct with the three humanizing mutations at Aβ amino acids 5, 10, and 13. The lower blot B indicates that the HET mice have significantly more amyloid peptide produced when directly compared to the wild-type murine form. Since the immuno-precipitation and blot were conducted using G2-10 antibody, this provides a direct comparison between the WT and HET animals. This data provide direct evidence for enhanced proteolytic processing of the NFEV (SEQ ID NO: 4) sequence compared to WT in the NFEV-hAPP heterozygote mice. Additionally, one can note an enhanced dimer band above the EV40 monomer standards compared to the Aβ40 standards, indicating the increased tendency of the EV amyloid peptide to aggregate compared to A040.

EXAMPLE 4

Amyloid 1-40 Measurements in Mouse Brain Extracts Using an Sandwich ELISA: Heterozygous Mice vs. WT Litter Mates ELISA Method Black 96 well plates (Corning, Cat# 3915) were coated with 100 ul of 10 ug/ml antibody 6E10 or normal mouse IgG as a control (Sigma, Cat# I-8765) in carbonate-bicarbonate buffer 0.05M at pH 9.6 (Sigma, Cat# C-3041) overnight. Plates were then washed 2× with 200 ul of PBS and blocked with 200 ul of 3% BSA/PBS for 2 hrs. 100 µl of either mouse brain extract (as prepared above in Example 3) or Aβ40 peptide standards (ranging from 6.25 pM-200 pM) were added to each well, followed by 50 μl of antibody G2-10 conjugated with alkaline phosphatase (AP) (1:500) in 3% BSA-PBS with Tween 0.3%. Aβ40 standards were spiked into wild type C57B116 brain homogenates prepared in a similar manner as samples in order to account for any matrix effects associated with the brain extracts and the ELISA reagents. Plates were incubated overnight with gentle rocking at 4° C. The next morning they were washed 5× with 200 μl of PBS with 0.05% Tween-20 (Bio-Rad, cat # 170-6531). 100 μl of AP substrate (Applied Biosystems, Cat# T2214) was added into each well and incubated at room temperature for 30 minutes. Luminescence of the substrate was then detected using an LJL Analyst plate reader (Molecular Devices). The concentrations of EV1-40 or Aβ 1-40 from each brain sample was then calculated based on either interpolation of (for WT litter mates and YAC mice) or extrapolation of (for heterozygous mice) the luminescent count for each animal from the standard curve.

Figure 2B:
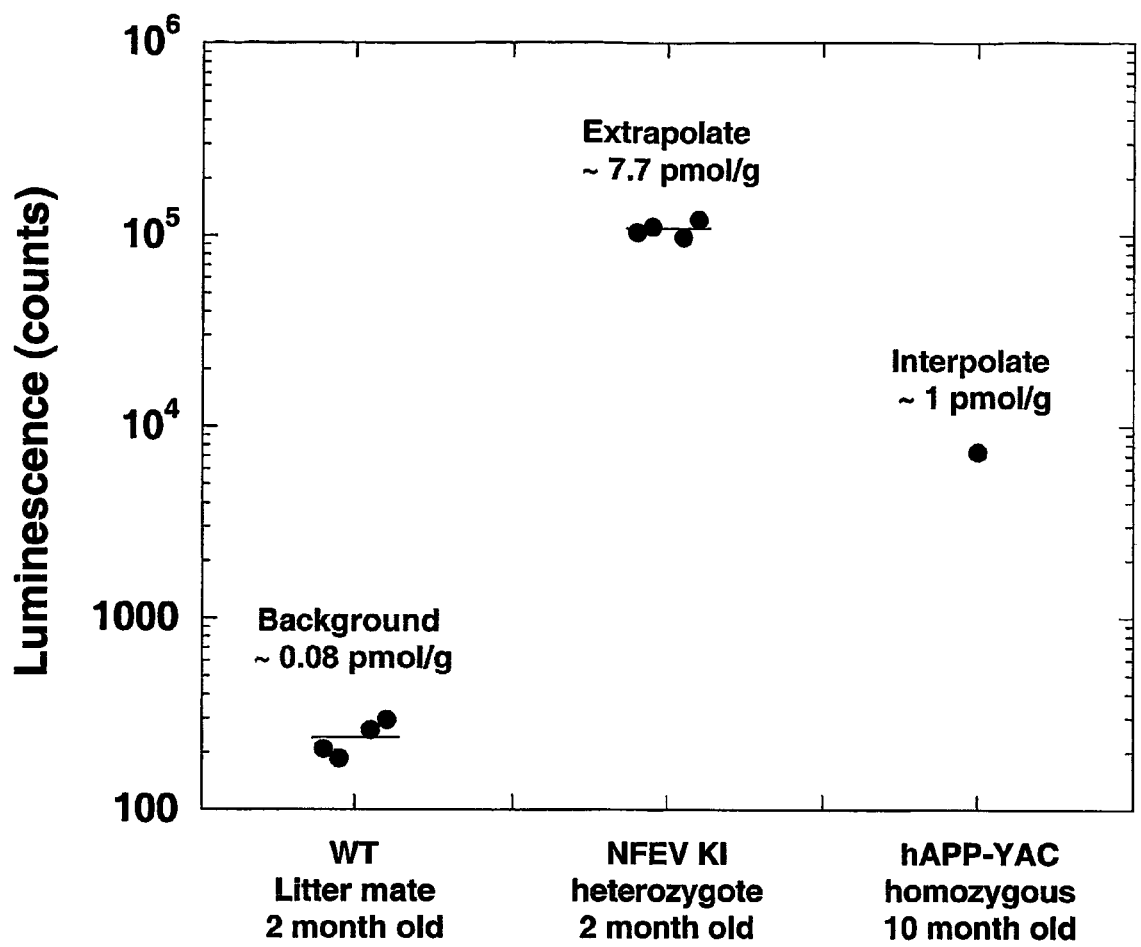

Quantitative analysis of the differences in Amyloid 1-40 cleavage product was performed using ELISA and Aβ 40 standards to determine the differences between the 3 mice strains. In FIG. 2A, one can see the average values from the six point standard curve, with the power law fit to the data. In FIG. 2B, one can see the scatterplot for the nine mouse brains analyzed. The values in pM on the x-axis of the standard curve were converted to fmol/g by multiplying by 11 to normalize concentration of amyloid 1-40 for total brain weight of sample.

The brains from 2 month old NFEV-hAPP KI mice show approximately 7 fold higher levels of EV Amyloid 1-40 product compared to the brains from 10 month old WT hAPP-Yac mice (FIG. 2B). On average, the NFEV KI mice produce about ~7.7 pmol/g (n=4) of EV Amyloid 1-40 compared to 1.0 pmol/g in the WT hAPP-Yac mice (n=1). One should note that the levels measured in the WT litter mates represents background signal of cross reactivity since the murine Aβ40 should not exhibit immuno-reactivity to the 6E10 antibody. Thus the NFEV-hAPP KI heterozygous mice exhibit significantly elevated levels of amyloid 1-40 cleavage products compared to the older WT hAPP-YAC mice in a sandwich ELISA based format as well.

EXAMPLE 5

Direct Western Comparison of sAPPβ and Amyloid Fragment in Heterozygous vs. WT Litter Mates vs WT hAPP-YAC Mice Direct Western Blot Analysis In addition to detection of the amyloid cleavage products, experiments were conducted to verify the NFEV hAPP KI amino acid sequence directly, using the anti-NF neo-epitope rabbit polyclonal antibody #2081. In particular, the secreted product of β secretase proteolytic cleavage of NFEV-hAPP, i.e. the N-terminal fragment of APP containing the NF neo-epitope at its c-terminus (sAPPβ-NF), was detected using antibody #2081.

Brain homogenates were prepared according to the methods described in Example 3 above. Rather than conduct an immunoprecipitation, 20 uL of each neutralized homogenate was loaded directly into the gel and run according the methods described above in Example 3. After blocking with reagent, the blotted membrane was then cut into two pieces horizontally around the 36 KD MW marker on the molecular weight ladder (the leftmost lane on the gel).

In order to detect the sAPPβ-NF fragment, the top half of the blotted membrane was incubated overnight with 1:1000 rabbit anti-NF neo-epitope antibody #2081 conjugated with alkaline phosphatase AP, in blocking agent with Tween 0.1%. The blot was washed, developed with an alkaline phosphatase substrate (Pierce, Cat# 34150) and exposed onto Biomax film (Kodak, Cat# 844 2907). In contrast, the lower portion of the same membrane was probed with the 6E10 antibody, which immuno-reacts with all human or humanized forms of the Aβ peptide around the 5, 10, and 13 amino acids.

In vivo β secretase cleavage of the replacement NFEV-hAPP KI protein leads to the formation of a secreted product of ~80-90 KD with the NF neo-epitope at its c-terminus (MW depends on degree of glycosylation). In order to confirm that the NFEV-APP construct is incorporated into the mouse genome and is also efficiently cleaved by endogenous β secretase the NF neo-epitope specific antibody #2081 was used to detect sAPPβ.

Figure 3:
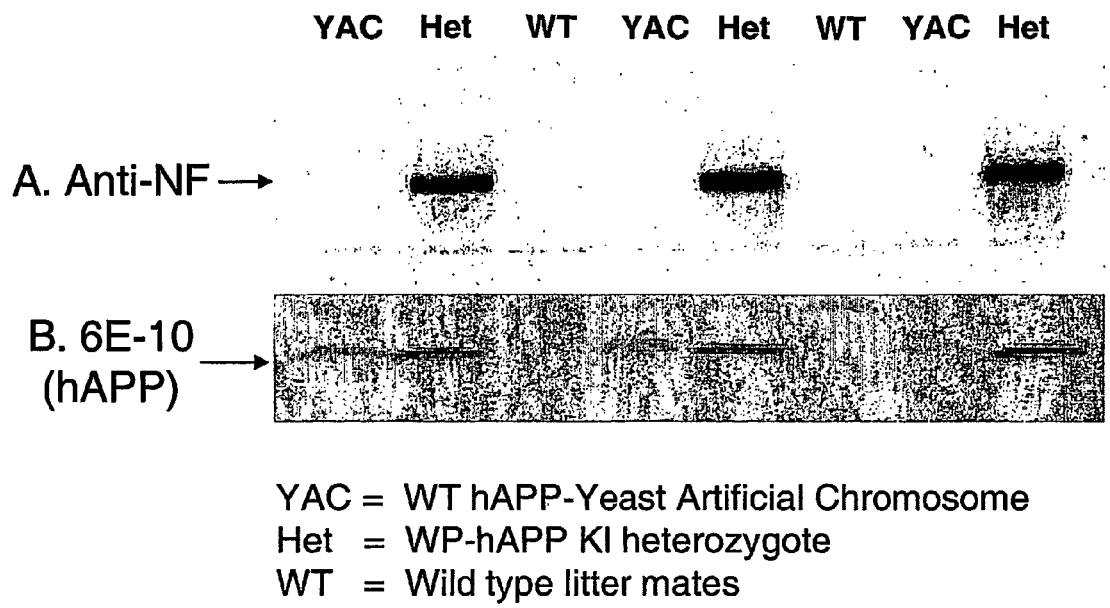
FIG. 3. Results from direct Western Blot analysis of DEA brain extracts of NFEV KI heterozygotes compared to wild type litter mates and APP-YAC mice. The gel was run and cut horizontally. In A. the blot was probed with an anti-NF rabbit polyclonal antibody 2080, confirming the immunoreactivity only in the heterozygous mice. In B. the blot was probed with 6E10 confirming the three humanizing mutations and showing the elevated levels of processed EV amyloid relative to the wt hAPP-YAC mice.
Figure 4:
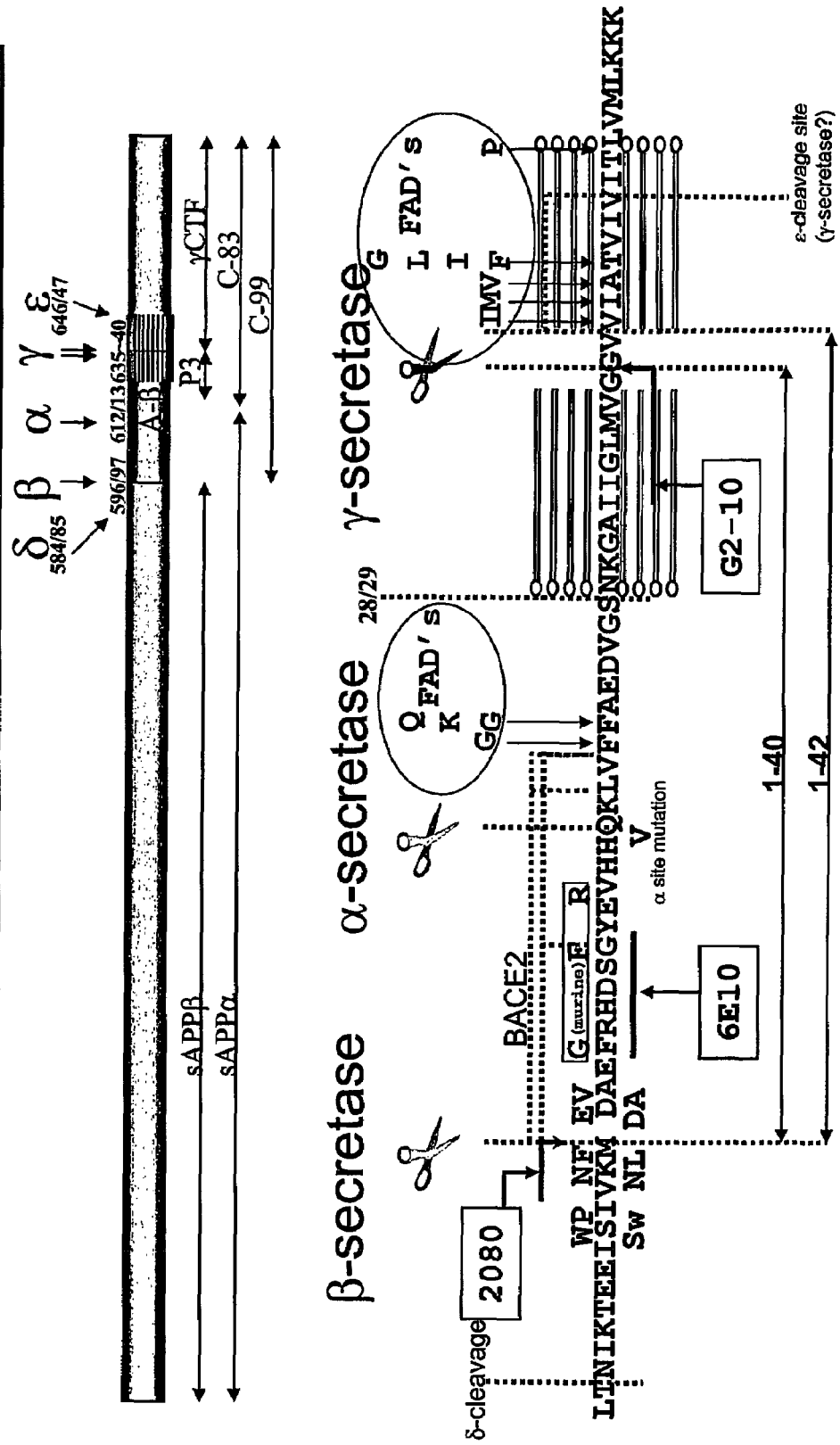
FIG. 4. Overview of APP695 showing the major cleavage sites along the molecule (SEQ ID NO: 4), including the α, β, and γ secretase sites in the upper portion. In the lower portion, one can see the amino acid sequence including any differing residues from Familial Alzheimer Disease as well as differences between murine and human Aβ. Finally, one is able to see the binding epitopes of the various antibodies used, including the neo-epitope specific antibodies 2080 and G2-10, as well as the capture antibody 6E10.

In FIG. 3A, using the anti-NF antibody #2081, detection of the β secretase N-terminal fragment (sAPPβ-NF) is only seen in the heterozygous mice and confirms the successful integration of the NFEV-APP construct into the mouse genome. Moreover, this offers additional evidence of appropriate processing by endogenous β secretase. Western analysis indicated that the NFEV-KI heterozygous mice indeed produce sAPPβ-NF as seen by the distinct band at ~80-90 Kd (FIG. 3A.). Importantly, no signal was detected in the WT litter mate brains and brains from WT hAPP overexpressed from a yeast artificial chromosome (WT hAPP-Yac mice) since they have the WT sequence which ends in the amino acids K and M. These results confirm that NFEV-APP is incorporated into the animal genome, is expressed and the resultant protein is efficiently processed by the endogenous β secretase.

Collectively, these data confirm that the NFEV-hAPP construct was successfully integrated into the mouse genome, was efficiently processed by endogenous β secretase and finally that the NFEV (SEQ ID NO: 4) mutation in APP leads to a profound increase in amyloid 1-40 peptide production, approximately 7 fold greater than in older WT hAPP-YAC mice. Thus, a novel genetically engineered knock-in animal model, where NFEV-APP is under control of endogenous promoter elements has been generated and provides an important animal model of Alzheimer's Disease.

EXAMPLE 6

Direct Western comparison of sAPPβ and Amyloid fragment in WT vs. Heterozygous vs. homozygous litter mates vs WT hAPP-YAC and APP-swe mice.

Direct Western Blot Analysis

Western analysis was conducted as indicated in Example 5 above. Brain homogenates were prepared according to the methods described in Example 3 above. After blocking with reagent, the blotted membrane was then probed by two color fluorescence detection on a LI-COR ODESSEY imager (LI-COR, LINCOLN, NE).

In order to detect the sAPPβ-NF fragment, the blotted membrane was incubated overnight with 1:1000 rabbit anti-NF neo-epitope antibody #2081 conjugated with one infrared dye, in blocking agent with Tween 0.1%. The blot was washed, and scanned on a LI-COR ODESSEY imager (LI-COR, LINCOLN, NE). Simultaneously, the same membrane was probed with the 6E10 antibody, which immuno-reacts with all human or humanized forms of the Aβ peptide around the 5, 10, and 13 amino acids.

In vivo β secretase cleavage of the replacement NFEV-hAPP KI protein leads to the formation of a secreted product of ~80-90 KD with the NF neo-epitope at its c-terminus (MW depends on degree of glycosylation). In order to confirm that the NFEV-APP construct is incorporated into the mice genome and is also efficiently cleaved by endogenous β secretase the NF neo-epitope specific antibody 2081 was used to detect sAPPβ.

Figure 5:
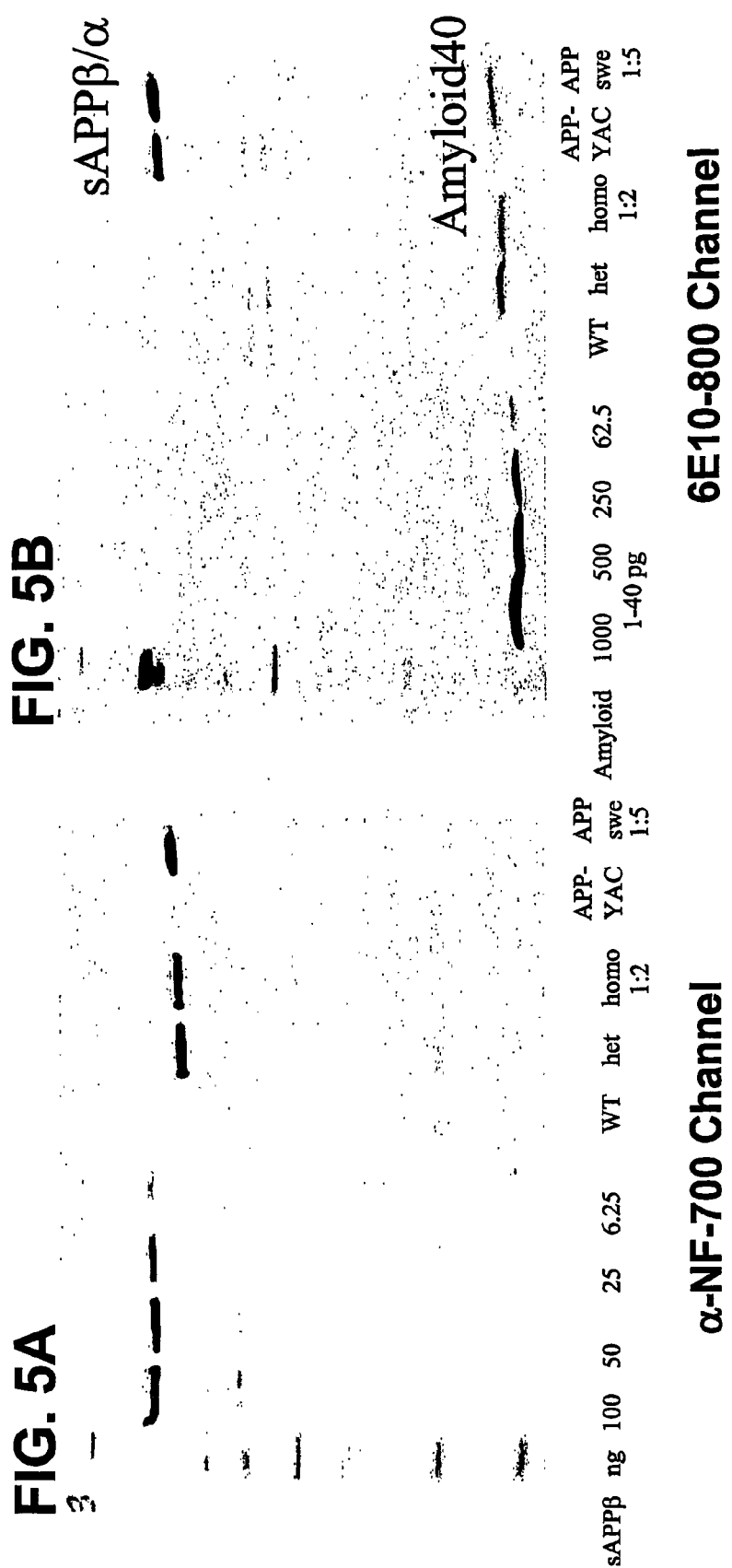
FIGS. 5A & B. Western blot analysis of nine week old heterozygous and homozygous NFEV-hAPP KI mice. One can see enhanced amyloid production in both heterozygous and homozygous mice relative to APP-YAC mice. Amyloid levels appear lower than that of age matched APP-Swe (Tg2576) controls. Enhanced processing by BACE is clearly seen in the sAPPbeta bands (see 5A) whereas the APP-YAC shows dominant alpha cleavage to form sAPPalpha (see 5B). APP-swe shows mixed processing of both sAPPbeta and sAPPalpha (see 5A & 5B).

In FIG. 5, using the anti-NF antibody 2081, detection of the β secretase N-terminal fragment (sAPPβ-NF) is only seen in the heterozygous and homozygous KI mice and confirms the successful integration of the NFEV-APP construct into the mouse genome. Moreover, this offers additional evidence of appropriate processing by endogenous β secretase. Western analysis indicated that the NFEV-KI mice indeed produce sAPPβ-NF as seen by the distinct band at ~80-90 Kd (FIG. 5). Importantly, no signal was detected in the WT litter mate brains and brains from WT hAPP overexpressed from a yeast artificial chromosome (WT hAPP-Yac mice) since they have the WT sequence which ends in the amino acids K and M. These results confirm that NFEV-APP is incorporated into the animal genome, is expressed and the resultant protein is efficiently processed by the endogenous β secretase.

EXAMPLE 7

Measurements in Mouse Brain Extracts Using a Sandwich ELISA: WT vs. Heterozygous Mice vs. Homozygous Litter Mates vs. APP-YAC vs. APP-Swe Mice.

ELISA Method

Figure 8:
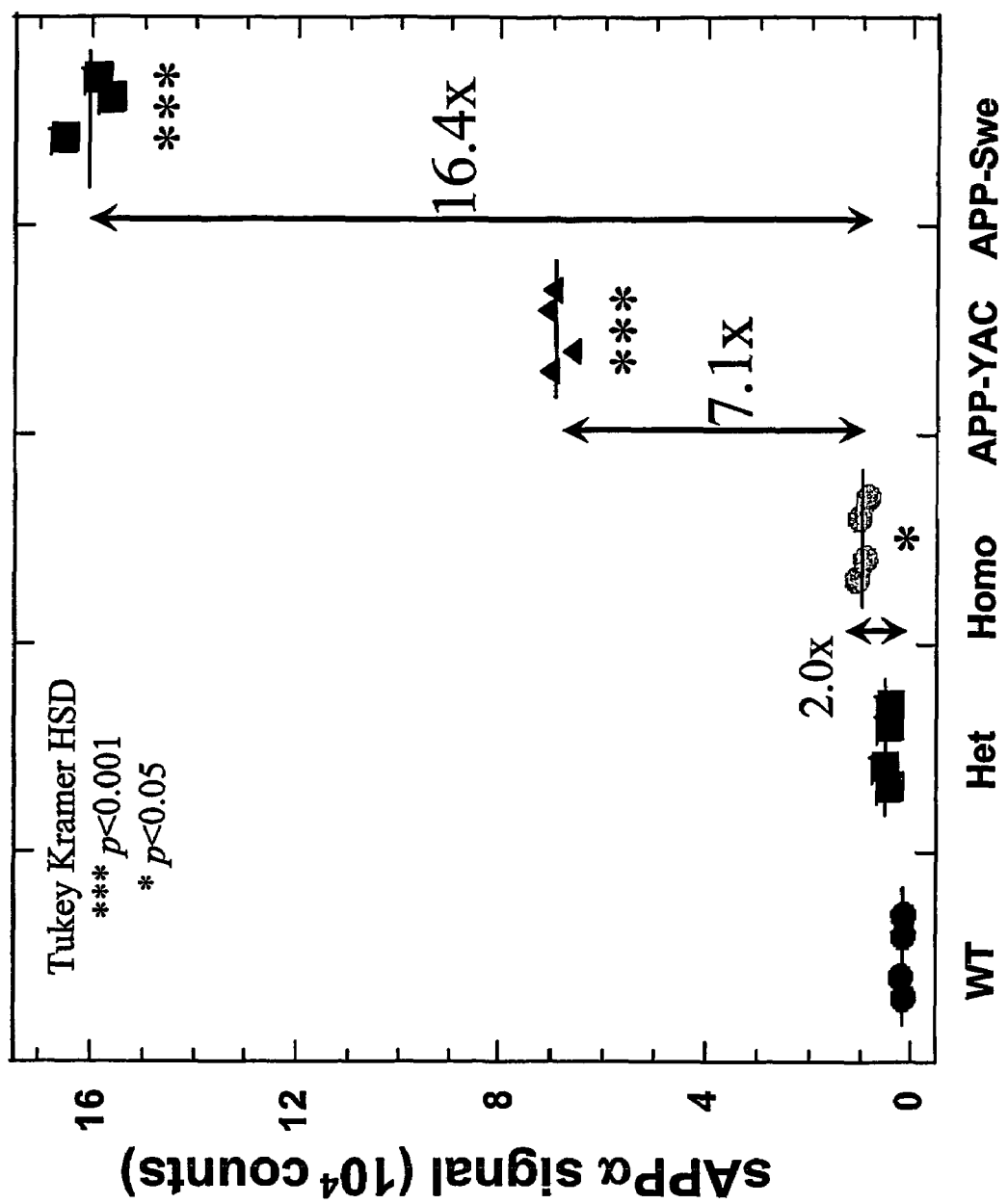
FIG. 8. Specific elevation of amyloid vs. sAPPalpha as a relevant model of human disease. A classic sandwich ELISA between antibodies 6E10 and 22C11-AP indicate roughly two fold increased production of sAPPbeta in homozygous versus heterozygous mice. In comparison, APP-YAC mice show roughly seven fold higher levels than homozygous animals; whereas, the homozygous animals are within a factor of 20 of aged matched APP-swe.

Samples were processed according to the methods of Example 4. ELISA antibody pairs were selected to measure sAPPbeta via 22C11-AP and α-NF neo-epitope antibody (FIG. 6), amyloid1-40 via 6E10 and G2-10-AP (FIG. H3), and sAPPalpha via 6E10 and 22C11-AP (FIG. 8).

Figure 6:
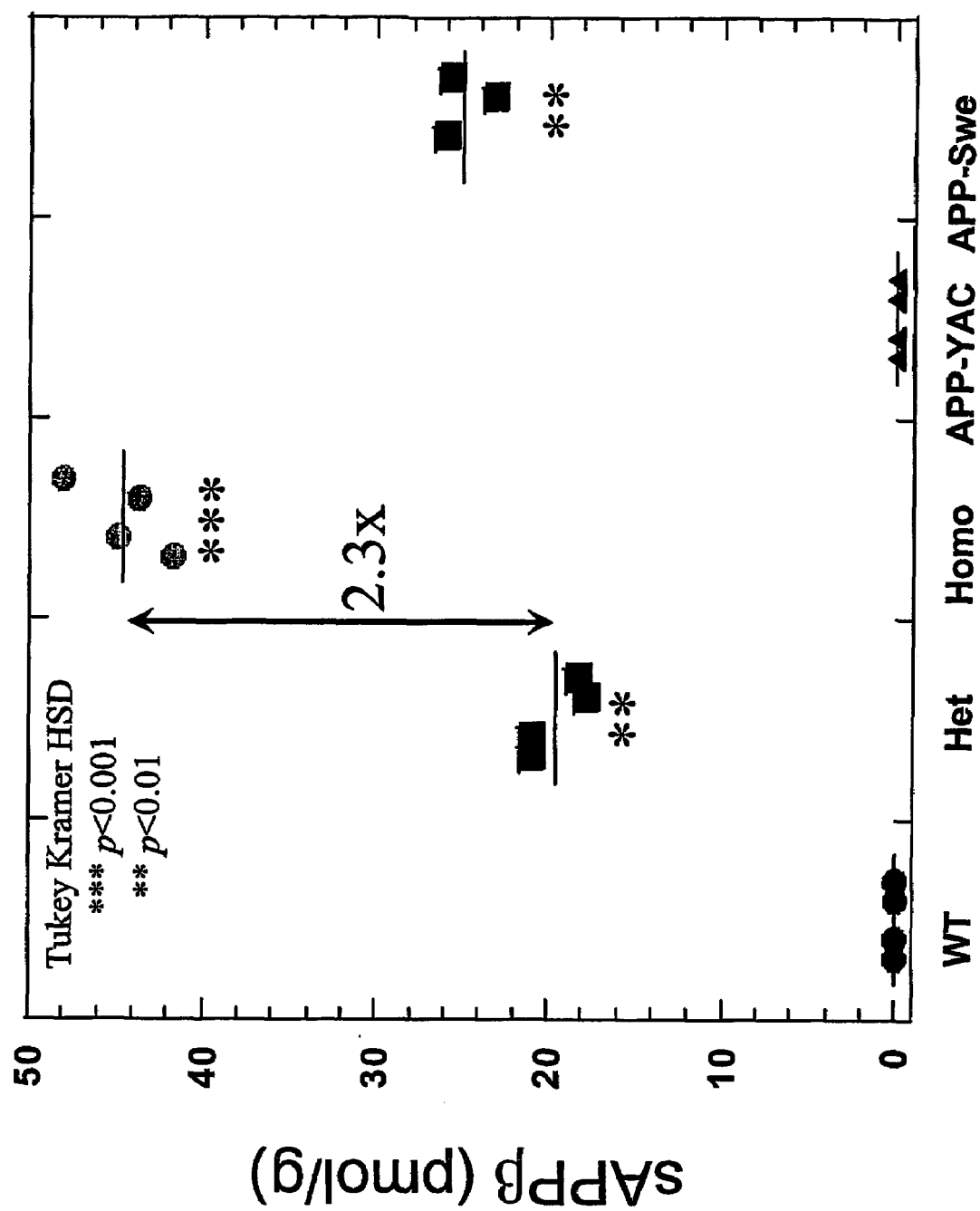
FIG. 6. Biochemical ELISA for sAPPbeta enables direct detection of BACE activity in a stoichiometric ratio. A classic sandwich ELISA between antibodies 22C11 and a-NF polyclonal antibody indicate roughly two fold increased production of sAPPbeta in homozygous versus heterozygous mice. In comparison, APP-YAC mice show little sAPPbeta whereas APP-swe mice show some cross-reactivity between the NF neo-epitope antibody and the sAPPbeta neo-epitope of the APP-swe mice.

Quantitative analysis of the differences in cleavage products were performed using ELISA and standards whenever available to determine the differences between the different strains of mice. In FIG. 6, one can see the scatterplot for the mouse brains analyzed.

The brains from 9 week old NFEV-hAPP KI homozygous mice show approximately 2 fold higher levels of sAPPbeta product compared to age-matched heterozygous animals. Some immuno-cross-reactivity can be observed with the APP-swe brain homogenates. This assay allows direct detection of BACE activity and is very useful in the direct assessment of in vivo BACE activity. Unlike assays which measure amyloid 140, this assay does not rely on gamma-secretase cleavage.

Figure 7:
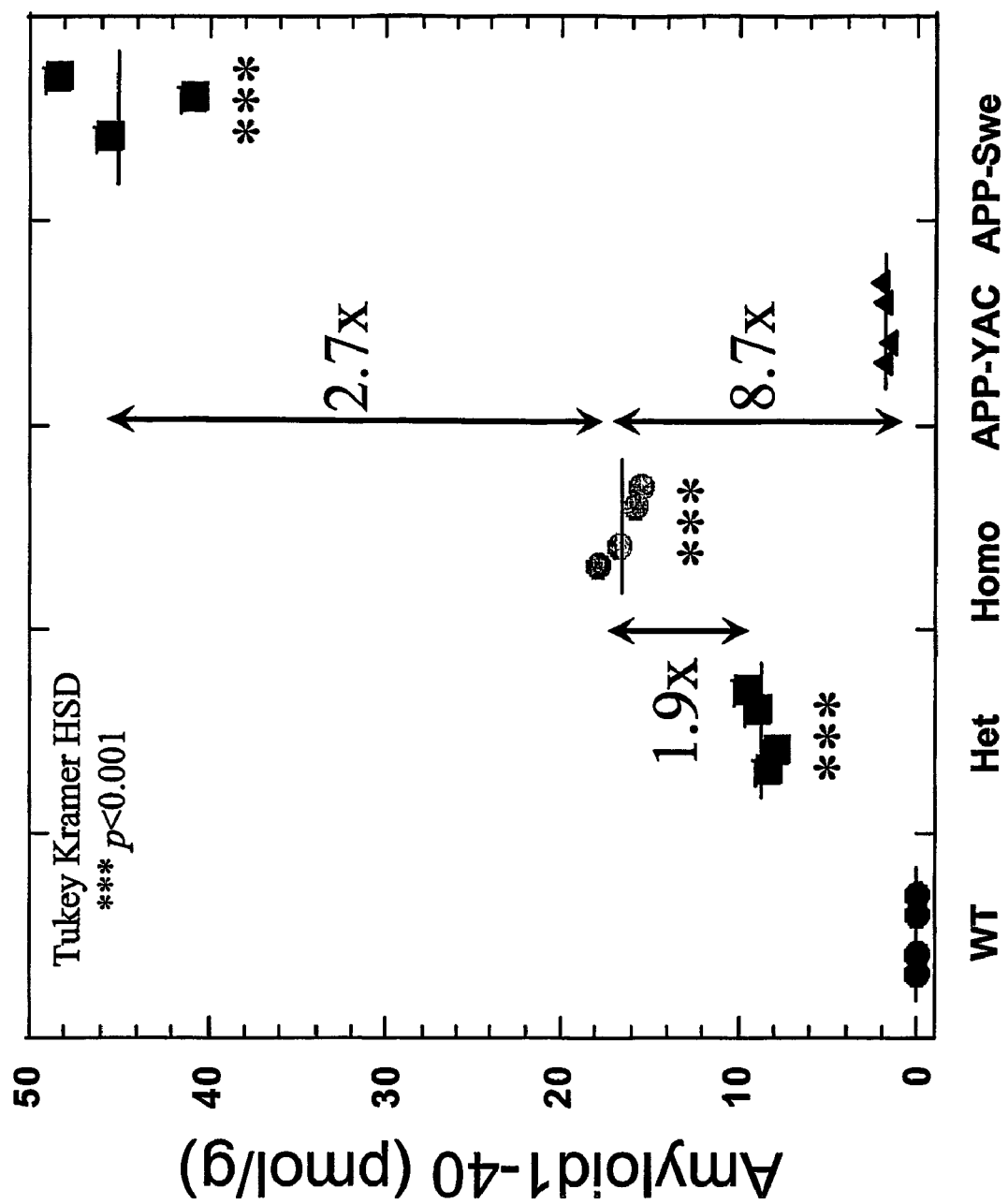
FIG. 7. Homozygous KI mice have twice as much amyloid as heterozygous KI mice and approximately 33% that of the APP-swe (Tg2576). A classic sandwich ELISA between antibodies 6E10 and G2-10-AP indicate roughly two fold increased production of amyloid1-40 in homozygous versus heterozygous mice. In comparison, APP-YAC mice show roughly nine fold lower levels than homozygous animals; whereas, the homozygous animals are within a factor of 3× of aged matched APP-swe.

Data presented in FIG. 7 shows nearly two fold elevated amyloid 1-40 in homozygous versus heterozygous KI mice. In comparison to APP-YAC, the homozygous animals have nearly nine fold higher levels of amyloid 140. Finally, compared to APP-swe, the homozygous animals exhibit under 3 fold less amyloid. This is a particularly striking result considering that the amyloid measured in the animals of the present invention was produced from endogenous levels of APP driven from the endogenous promoter and not from APP overexpressed from a high level promoter like the prion promoter in the APP-swe (Tg2576) mouse.

Figure 9:
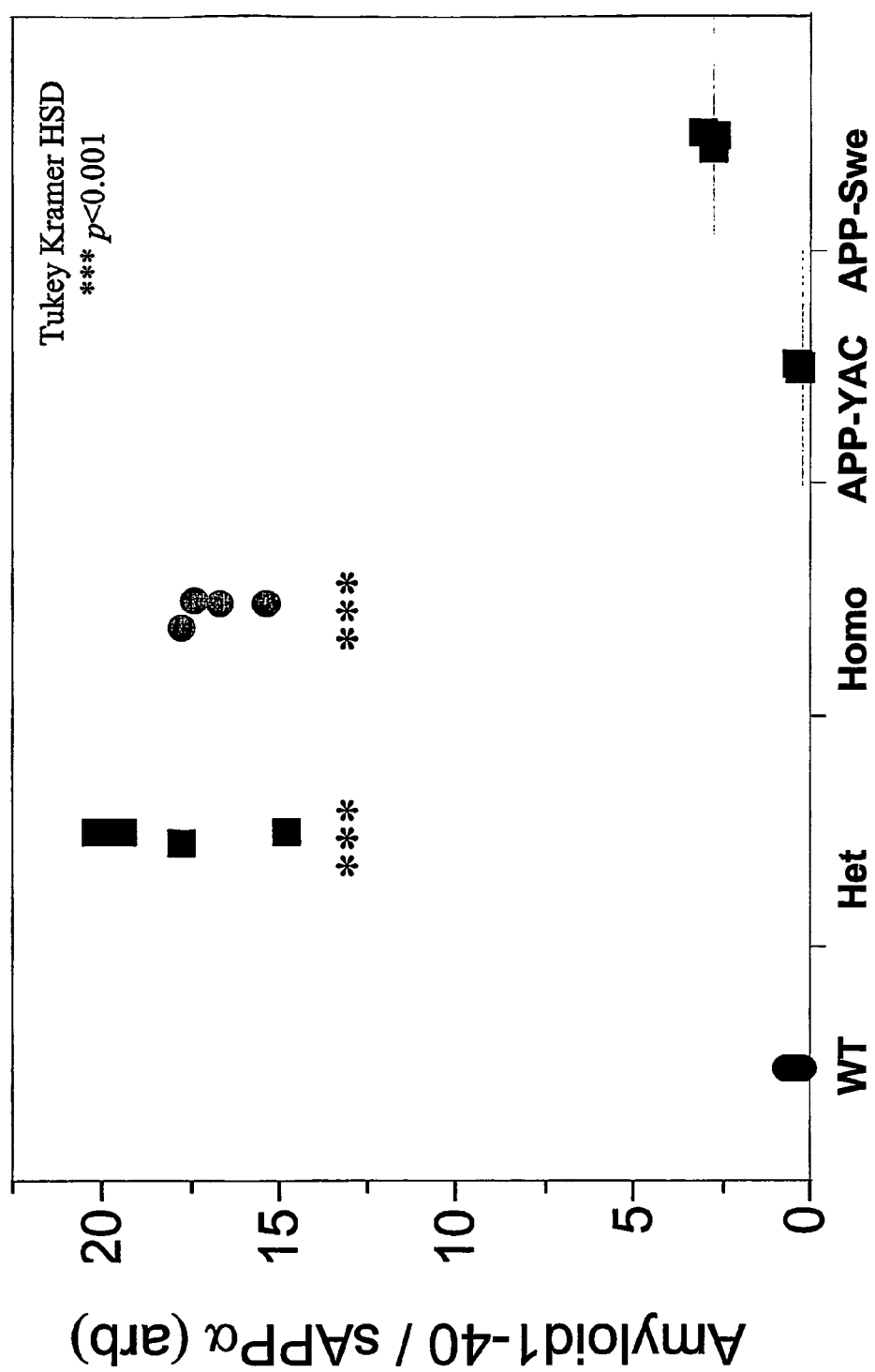
FIG. 9. Enhanced cleavage rather than enhanced substrate production as a useful animal model. Both heterozygous and homozygous KI mice exhibit roughly 15-20 fold increases in BACE processing versus alpha processing as measured by amyloid1-40/sAPPalpha activity.

The data presented in FIG. 8 demonstrates that alpha secretase activity is much greater in APP-YAC and APP-swe mice than in the mice of the present invention. The ratio of amyloid 1-40 divided by sAPPalpha shows enhanced activity through the BACE/gamma-secretase pathway compared to the alpha-secretase/gamma-secretase pathway (see FIG. 9). This enhancement is reflective of human AD in which the abundance and activity of BACE is elevated in post-mortem Aβ patients compared to age-matched controls. The animal of the present invention provides not only a model for the direct in vivo monitoring of BACE activity via the sAPPbeta sandwich ELISA, but also a relevant model of human disease. Amyloid production is increased due to substrate cleavage, rather than over expression of APP substrate.

What is claimed is:

1. A transgenic mouse all of whose germ and somatic cells compromise at least one allele carrying a gene encoding an amyloid precursor protein wherein the amino acids flanking the β-secretase cleavage site are NF and EV, wherein the mouse exhibits an increase in the production of Aβ when compared to a wild-type animal.

2. The transgenic mouse of claim 1, wherein the mouse is heterozygous for said allele.

3. The transgenic mouse of claim 1 wherein the mouse is homozygous for said allele.

4. The transgenic mouse of claim 1 wherein said amyloid precursor protein is selected from the group consisting of a murine protein, a human protein and a humanized protein.

5. The transgenic mouse of claim 1 wherein said amyloid precursor protein further comprises a mutation associated with a Familial Alzheimer's Disease.

6. The transgenic mouse of claim 5 wherein the mutation affects cleavage of the amyloid precursor protein at the β-secretase cleavage site.

7. The transgenic mouse of claim 5 wherein the mutation affects cleavage of the amyloid precursor protein at the β-secretase cleavage site.

8. The transgenic mouse of claim 1 wherein said mouse further comprises a second transgene associated with Alzheimer's Disease selected from the group consisting of presenillin-1, tau, α-synuclein and β-secretase.

9. The transgenic mouse of claim 1 wherein all of whose germ and somatic cells lack a functional gene for β-secretase.

10. A tissue derived from the mouse of claim 1.

11. The tissue of claim 10 which is selected from the group consisting of brain, brain slices, plasma, cerebrospinal fluid and pancreatic tissue.

12. An in vivo method for screening a candidate compound that is potentially useful for the treatment or prevention of Alzheimer's disease which comprises:

(a) administering a candidate drug to the transgenic mouse of claim 1, (b) measuring the level of Aβ peptide produced in the mouse, (c) comparing the level of Aβ peptide production measured in step (b) to the level of Aβ produced in a control mouse which has not contacted the candidate drug, and (d) determining whether the candidate compound reduces the level of Aβ peptide produced.

13. A cell line derived from a mouse of claim 1.

14. The cell line of claim 13 selected from the group consisting of glial cell lines, neuronal cell lines and fibroblast cell lines.

15. The transgenic mouse of claim 1 wherein the amyloid precursor protein is expressed from the native amyloid precursor protein promoter.

16. The transgenic mouse of claim 15 wherein the mouse exhibits a wild-type pattern of spatial and temporal expression of amyloid precursor protein and an increase in β-secretase cleavage of amyloid precursor protein when compared to a wild-type animal.

17. The transgenic mouse of claim 15 wherein the animal exhibits an increase in the ratio of β-secretase cleavage over α-secretase cleavage when compared to a wild-type animal.

18. The transgenic mouse of claim 15 wherein the mouse exhibits an increase in β-secretase cleavage of amyloid precursor protein and an increase in production of Aβ amyloid when compared to a wild-type animal.

* * * * *

SEQUENCE LISTING

```
<160> NUMBER OF SEQ ID NOS: 13

<210> SEQ ID NO 1
<211> LENGTH: 10
<212> TYPE: PRT
<213> ORGANISM: mus musculus

<400> SEQUENCE: 1

Ser Glu Val Asn Leu Asp Ala Glu Phe Arg
1               5                   10

<210> SEQ ID NO 2
<211> LENGTH: 7
<212> TYPE: PRT
<213> ORGANISM: mus musculus

<400> SEQUENCE: 2

Val Asn Leu Ala Ala Glu Phe
1               5

<210> SEQ ID NO 3
<211> LENGTH: 8
<212> TYPE: PRT
<213> ORGANISM: mus musculus
```

```
<400> SEQUENCE: 3

Glu Val Asn Leu Ala Ala Glu Phe
 1               5

<210> SEQ ID NO 4
<211> LENGTH: 4
<212> TYPE: PRT
<213> ORGANISM: mus musculus

<400> SEQUENCE: 4

Asn Phe Glu Val
 1

<210> SEQ ID NO 5
<211> LENGTH: 69
<212> TYPE: PRT
<213> ORGANISM: mus musculus

<400> SEQUENCE: 5

Leu Thr Asn Ile Lys Thr Glu Glu Ile Ser Ile Val Lys Met Asp Ala
 1               5                  10                  15

Glu Phe Arg His Asp Ser Gly Tyr Glu Val His His Gln Lys Leu Val
             20                  25                  30

Phe Phe Ala Glu Asp Val Gly Ser Asn Lys Gly Ala Ile Ile Gly Leu
         35                  40                  45

Met Val Gly Gly Val Val Ile Ala Thr Val Ile Val Ile Thr Leu Val
     50                  55                  60

Met Leu Lys Lys Lys
 65

<210> SEQ ID NO 6
<211> LENGTH: 4
<212> TYPE: PRT
<213> ORGANISM: mus musculus

<400> SEQUENCE: 6

Lys Met Asp Ala
 1

<210> SEQ ID NO 7
<211> LENGTH: 4
<212> TYPE: PRT
<213> ORGANISM: mus musculus

<400> SEQUENCE: 7

Asn Leu Asp Ala
 1

<210> SEQ ID NO 8
<211> LENGTH: 80
<212> TYPE: DNA
<213> ORGANISM: mus musculus

<400> SEQUENCE: 8
gaagagatct cggaagtgaa cttcgaagtg gaattccgac atgattcagg atatgaagtc    60
catcatcaaa aactggtagg                                                80

<210> SEQ ID NO 9
<211> LENGTH: 25
<212> TYPE: DNA
<213> ORGANISM: mus musculus
```

```
<400> SEQUENCE: 9
ttttgaccca tatagaacat gtccc                                            25

<210> SEQ ID NO 10
<211> LENGTH: 22
<212> TYPE: DNA
<213> ORGANISM: mus musculus

<400> SEQUENCE: 10
gcacattaaa ttcatggcac cc                                               22

<210> SEQ ID NO 11
<211> LENGTH: 20
<212> TYPE: DNA
<213> ORGANISM: mus musculus

<400> SEQUENCE: 11
cctttccctc cctccccttt                                                  20

<210> SEQ ID NO 12
<211> LENGTH: 21
<212> TYPE: DNA
<213> ORGANISM: mus musculus

<400> SEQUENCE: 12
ggaaactggg accacctcta a                                                21

<210> SEQ ID NO 13
<211> LENGTH: 5
<212> TYPE: PRT
<213> ORGANISM: mus musculus

<400> SEQUENCE: 13

Ser Glu Val Asn Phe
  1               5
```